United States Patent
Oster et al.

(10) Patent No.: US 8,700,118 B2
(45) Date of Patent: Apr. 15, 2014

(54) BIOMEDICAL SENSOR SYSTEM

(75) Inventors: Craig D. Oster, Oakdale, MN (US); Hatim M. Carim, West St. Paul, MN (US); Casey L. Carlson, Edina, MN (US); Vinod P. Menon, Woodbury, MN (US); Jon A. Kirschhoffer, White Bear Lake, MN (US); William Bedingham, Woodbury, MN (US); Christopher R. Yungers, Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 431 days.

(21) Appl. No.: 12/990,064

(22) PCT Filed: Apr. 29, 2009

(86) PCT No.: PCT/US2009/042013
§ 371 (c)(1),
(2), (4) Date: Dec. 1, 2010

(87) PCT Pub. No.: WO2009/134826
PCT Pub. Date: Nov. 5, 2009

(65) Prior Publication Data
US 2011/0077497 A1    Mar. 31, 2011

Related U.S. Application Data

(60) Provisional application No. 61/049,671, filed on May 1, 2008.

(51) Int. Cl.
*A61B 5/0408*   (2006.01)
*A61B 5/00*     (2006.01)

(52) U.S. Cl.
USPC ........... 600/372; 600/391; 600/393; 600/473; 600/476

(58) Field of Classification Search
USPC .................................................. 600/393, 372
See application file for complete search history.

(56) References Cited

U.S. PATENT DOCUMENTS

| 3,004,229 A | 10/1961 | Stearns |
| 3,805,769 A | 4/1974  | Sessions |

(Continued)

FOREIGN PATENT DOCUMENTS

| EP | 0122085 | 6/1987 |
| EP | 0282307 | 9/1988 |

(Continued)

OTHER PUBLICATIONS

Brosteaux, "Design and Fabrication of Elastic Interconnections for Streatchable Electronic Circuits", IEEE Electron Device Letters, Jul. 2007, vol. 28, No. 7, pp. 552-554.

(Continued)

*Primary Examiner* — Lee S Cohen
(74) *Attorney, Agent, or Firm* — Thomas M. Spielbauer; Kevin Weber

(57) ABSTRACT

A biomedical sensor system. The system can include a sensor adapted to create a signal based on a physiological characteristic from a subject, and a hub adapted to receive the signal from the sensor. The signal can include at least one of an electromagnetic signal, an electrical signal, an acoustic signal, a mechanical signal, a thermal signal, and a chemical signal. The system can further include a connector adapted to couple the sensor and the hub, the connector having a variable length, such that the sensor and the hub can be positioned a variable distance apart by changing the length of the connector. The connector can be adapted to provide a pathway between the sensor and the hub for the signal. A method of applying a biomedical sensor system to a subject can include changing the length of the variable-length connector to provide an appropriate distance between the sensor and the hub, and coupling the sensor to the subject.

18 Claims, 8 Drawing Sheets

(56) References Cited

U.S. PATENT DOCUMENTS

| | | | |
|---|---|---|---|
| 3,845,757 A | 11/1974 | Weyer | |
| 4,199,209 A | 4/1980 | Cherian | |
| 4,330,165 A | 5/1982 | Sado | |
| 4,402,562 A | 9/1983 | Sado | |
| 4,520,562 A | 6/1985 | Sado | |
| 4,524,087 A | 6/1985 | Engel | |
| 4,527,087 A | 7/1985 | Taya | |
| 4,539,996 A | 9/1985 | Engel | |
| 4,554,924 A | 11/1985 | Engel | |
| 4,640,289 A | 2/1987 | Craighead | |
| 4,694,835 A | 9/1987 | Strand | |
| 4,715,382 A | 12/1987 | Strand | |
| 4,771,783 A | 9/1988 | Roberts | |
| 4,846,185 A | 7/1989 | Carim | |
| 4,848,353 A | 7/1989 | Engel | |
| 5,012,810 A | 5/1991 | Strand | |
| 5,133,356 A | 7/1992 | Bryan | |
| 5,215,087 A | 6/1993 | Anderson | |
| 5,226,225 A | 7/1993 | Bryan | |
| 5,296,079 A | 3/1994 | Romo | |
| 5,338,490 A | 8/1994 | Dietz | |
| 5,341,806 A | 8/1994 | Gadsby | |
| 5,385,679 A | 1/1995 | Uy | |
| 5,427,535 A | 6/1995 | Sinclair | |
| 5,511,553 A | 4/1996 | Segalowitz | |
| 5,516,581 A | 5/1996 | Kreckel | |
| 5,660,178 A | 8/1997 | Kantner | |
| 5,672,402 A | 9/1997 | Kreckel | |
| 5,779,632 A | 7/1998 | Dietz | |
| 5,813,979 A | 9/1998 | Wolfer | |
| 5,816,848 A | 10/1998 | Zimmerman | |
| 5,989,708 A | 11/1999 | Kreckel | |
| D425,203 S | 5/2000 | Sheehan | |
| 6,106,305 A | 8/2000 | Kozel | |
| 6,168,442 B1 | 1/2001 | Naoi | |
| 6,205,346 B1 | 3/2001 | Akiva | |
| D443,063 S | 5/2001 | Pisani | |
| 6,231,962 B1 | 5/2001 | Bries | |
| D445,507 S | 7/2001 | Pisani | |
| 6,286,208 B1 | 9/2001 | Shih | |
| 6,289,238 B1 | 9/2001 | Besson | |
| 6,312,393 B1 | 11/2001 | Abreu | |
| 6,327,507 B1 | 12/2001 | Buchan | |
| 6,385,473 B1 | 5/2002 | Haines | |
| 6,403,206 B1 | 6/2002 | Bries | |
| 6,411,834 B1* | 6/2002 | Nagai | 600/348 |
| 6,447,308 B1 | 9/2002 | McCarthy | |
| 6,494,829 B1 | 12/2002 | New, Jr. | |
| 6,527,900 B1 | 3/2003 | Kreckel | |
| 6,572,945 B2 | 6/2003 | Bries | |
| 6,577,893 B1 | 6/2003 | Besson | |
| 6,611,705 B2 | 8/2003 | Hopman | |
| 6,830,549 B2 | 12/2004 | Bui | |
| D501,558 S | 2/2005 | Chastain | |
| D505,206 S | 5/2005 | Chastain | |
| 7,136,691 B2 | 11/2006 | Menon | |
| 7,197,357 B2 | 3/2007 | Istvan | |
| 7,215,991 B2 | 5/2007 | Besson | |
| 7,362,087 B2 | 4/2008 | Kimura | |
| 8,180,425 B2* | 5/2012 | Selvitelli et al. | 600/382 |
| 2001/0019764 A1 | 9/2001 | Bries | |
| 2003/0122021 A1 | 7/2003 | McConnell | |
| 2004/0236202 A1 | 11/2004 | Burton | |
| 2005/0251003 A1* | 11/2005 | Istvan et al. | 600/393 |
| 2007/0027388 A1* | 2/2007 | Chou | 600/393 |
| 2007/0279217 A1 | 12/2007 | Venkatraman | |
| 2007/0299325 A1 | 12/2007 | Farrell | |
| 2008/0058614 A1 | 3/2008 | Banet | |
| 2008/0097908 A1 | 4/2008 | Dicks | |
| 2008/0097909 A1 | 4/2008 | Dicks | |
| 2008/0097910 A1 | 4/2008 | Dicks | |
| 2008/0097911 A1 | 4/2008 | Dicks | |
| 2008/0097912 A1 | 4/2008 | Dicks | |
| 2008/0097913 A1 | 4/2008 | Dicks | |
| 2008/0097914 A1 | 4/2008 | Dicks | |
| 2008/0097917 A1 | 4/2008 | Dicks | |

FOREIGN PATENT DOCUMENTS

| | | |
|---|---|---|
| EP | 0875222 | 11/1998 |
| GB | 2058652 | 4/1981 |
| JP | 2004-215964 | 8/2004 |
| WO | WO 02-47737 | 6/2002 |
| WO | WO 2009-134823 | 11/2009 |

OTHER PUBLICATIONS

"Emissivity control Coatings", NanoSonic, Inc. Blackburg, Virginia, USA [Online],(date unknown but believed to be prior to the date of the filing of the present application), [retrived from internet on Apr. 15, 2008], URL <http://www.nanosonic.com/>, pp. 1-2.

Ruksakulpiwat, "Comparative study of structure and property of ziegler-natta and metallocene based linear low density polyethylene in injection moldings" School of Polymer Engineering Tech.Papers, 2001, 582-586.

"Stretchable and Elastic Electronics and Sensor Circuits @ TFCG Microsystems Lab", Ghent University,Belgium [Online],[updated on the internet on Nov. 7, 2007], [retrived from internet on Apr. 15, 2008], URL <http://tfcg.elis.ugent.be/projects/stretchable.html>, pp. 1-7.

"Why the LifeSync® System?", LifeSync Corporation [Online], [Updated on the internet on Feb. 1, 2008], [retrived from internet on Apr. 15, 2008], URL <http://www.lifesynccorp.com/healthcareproviders/why-lifesync.html>, pp. 1-10.

International Search Report for PCT/US2009/042013, mailed Jun. 24, 2009, 3 pages.

Written Opinion for PCT/US2009/042013, mailed Jun. 24, 2009, 8 pages.

International Search Report for PCT/US2009/042010, mailed Jan. 4, 2010, 6 pages.

Written Opinion for PCT/US2009/042010, mailed Jun. 4, 2010, 9 pages.

Sybil P. Parker, McGraw-Hill Dictionary of Scientific and Technical Terms—Fifth Edition, McGraw-Hill, Inc., New York, NY, 1994, ISBN0-07-042333-4, p. 1523.

McGraw-Hill Encyclopedia of Science and Technology—6th Edition, McGraw-Hill Book Company, New York, NY, 1987, p. 35.

Office Action dated Aug. 30, 2012, in U.S. Appl. No. 12/990,057, 12 pgs.

Supplementary European Search Report, Apr. 20, 2013.

* cited by examiner

BIOMEDICAL SENSOR SYSTEM

CROSS REFERENCE TO RELATED APPLICATIONS

This application is a national stage filing under 35 U.S.C. 371 of PCT/US2009/042013, filed Apr. 29, 2009, which claims priority to provisional Application No. 61/049,671, filed May 1, 2008, the disclosures of which are incorporated by reference in their entirety herein.

FIELD

The present disclosure generally relates to a biomedical sensor system, and particularly, to a biomedical sensor system comprising connectors of variable length.

BACKGROUND

Therapeutic and diagnostic medical procedures utilize equipment capable of processing signals that are received from a subject or are delivered to a subject. In these procedures, the interface between the subject and the applicable equipment typically includes a sensor. Some sensors, for example, are in the form of electrodes constructed to include a conductor connected electrically to the medical equipment and a conductive medium that is adapted for contact (e.g., with an adhesive) with the subject (e.g., a subject's skin).

SUMMARY

Some embodiments of the present disclosure provide a biomedical sensor system. The system can include a sensor adapted to create a signal based on a physiological characteristic from a subject, and a hub adapted to receive the signal from the sensor. The signal can include at least one of an electromagnetic signal, an electrical signal, an acoustic signal, a mechanical signal, a thermal signal, a chemical signal, and combinations thereof. The system can further include a connector adapted to couple the sensor and the hub, the connector having a variable length, such that the sensor and the hub can be positioned a variable distance apart by changing the length of the connector. The connector can be adapted to provide a pathway between the sensor and the hub for the signal.

In some embodiments of the present disclosure, a biomedical sensor system is provided. The system can include a hub, a sensor adapted to create a signal based on a physiological characteristic from a subject, and a connector. The signal can include at least one of an electromagnetic signal, an electrical signal, an acoustic signal, a mechanical signal, a thermal signal, a chemical signal, and combinations thereof. The connecter can be coupled to the sensor and can be adapted to be further coupled to the hub to provide a pathway between the hub and the first sensor for the signal. The connector can have a variable length.

Some embodiments of the present disclosure provide a method of applying a biomedical sensor system to a subject. The method can include providing a biomedical sensor system comprising a hub, a sensor, and a variable-length connector. The connector can be positioned to couple the sensor and the hub and can be adapted to provide a pathway between the hub and the sensor for at least one of an electromagnetic signal, an electrical signal, an acoustic signal, a mechanical signal, a thermal signal, a chemical signal, and combinations thereof. The method can further include changing the length of the variable-length connector to provide an appropriate distance between the sensor and the hub, and coupling the sensor to the subject.

Other features and aspects of the present disclosure will become apparent by consideration of the detailed description and accompanying drawings.

DETAILED DESCRIPTION

Figure 1:
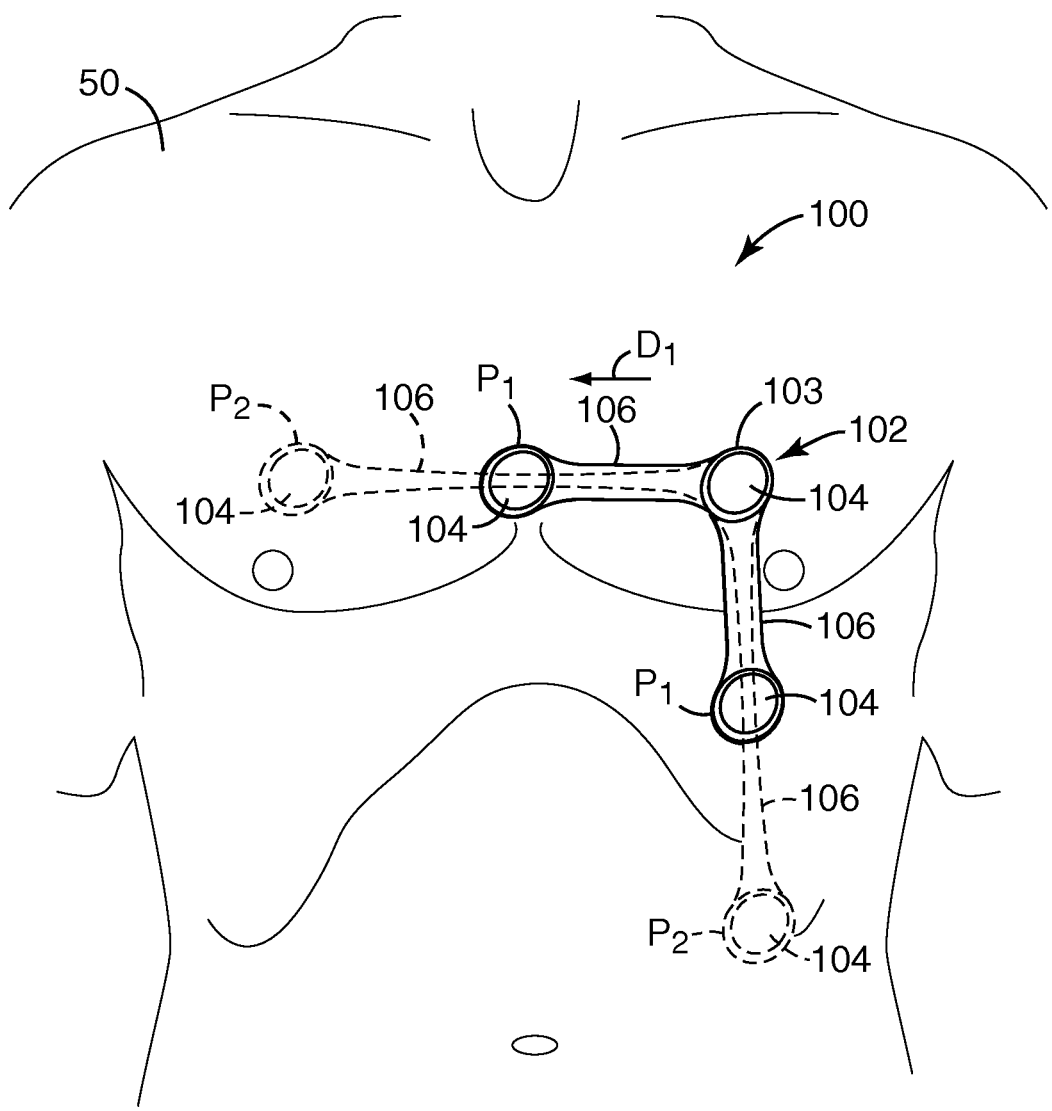
FIG. 1 is a top plan view of a biomedical sensor system according to one embodiment of the present disclosure, shown positioned on a subject.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected," and "coupled" and variations thereof are used broadly and encompass both direct and indirect connections, and couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to a biomedical sensor system. By way of example, a biomedical sensor system (e.g., where one or more sensors include electrodes) can be employed in diagnostic procedures and equipment that include electrocardiography for monitoring heart activity and diagnosing heart abnormalities, electroencephalography for monitoring brain activity and diagnosing brain abnormalities, and electromyography for monitoring the physiological properties of muscles at rest and in contraction. A biomedical sensor system can also be employed in therapeutic procedures and equipment such as in transcutaneous electronic nerve stimulation (TENS) devices that are used for pain management; neuromuscular stimulation (NMS) techniques for the treatment of certain conditions such as scoliosis; defibrillation devices for dispensing electrical energy to a subject (e.g., to defibrillate the heart); and dispersive devices that receive electrical energy that has been applied to an incision made during electrosurgery.

In addition, a biomedical sensor system can be employed in telemetry and remote monitoring by using technologies that allow data to be transmitted from a sensor coupled to a subject to a receiver that will further manipulate and process the data. Such telemetric and remote monitoring devices include, for example, ambulatory devices, such as a Holter monitor. During remote monitoring, the subject can be continuously monitored over a period of time, sometimes ranging on the scale of days or weeks. In such telemetry and ambulatory applications, providing site accurate application of the biomedical sensors can be important for accurate data accumulation and subject comfort during normal routine activities.

In general, the biomedical sensor system of the present disclosure is size-configurable, which can allow accommodation of a variety of subject sizes. Accommodating a variety of subject sizes can improve the accuracy of the diagnostic and/or therapeutic procedure being employed, and can enhance subject comfort. Such size-configurable constructions can also optimize signal generation (e.g., in monitoring/diagnostic applications), and can reduce the waste created in manufacturing such constructions. Such size-configurable constructions can further exhibit a low profile with minimal slack between components, which can enhance safety and subject comfort.

The biomedical sensor system of the present disclosure can be adapted to create one or more signals based on one or more physiological characteristics. A variety of forms of energy can be sensed by one or more sensors of the biomedical sensor system and converted into one or more signals for processing (e.g., in monitoring/diagnostic applications), or the sensor can be used to deliver a variety of forms of energy to a subject (e.g., in therapeutic applications). Whether the sensors are receiving and/or delivering energy to the subject, the sensors can function as transducers to convert one type of energy to another.

In addition to being adapted to create one or more signals based on one or more physiological characteristics, the biomedical sensor system can be adapted to communicate and/or take action to alter one or more characteristics of devices (e.g., sensors) of the system. For example, in some embodiments, the biomedical sensor system can be adapted to increase the filtering frequency content of signals if the system detects noise of such undesirable frequencies in the desired monitored signal.

Examples of suitable forms of signals that can be created and/or converted by the biomedical sensor system of the present disclosure include, but are not limited to, electromagnetic signals (e.g., optical signals), heat (i.e., a thermal signal), electrical signals, acoustic signals, mechanical signals, chemical signals, and combinations thereof. Examples of suitable sensors can include, but are not limited to, an electrode (e.g., a sensing electrode, a defibrillation electrode, a dispersive electrode, etc.); an accelerometer; a thermocouple, sensors for sensing one or more of blood oxygen saturation, glucose, body temperature, blood pressure; other suitable sensors; and combinations thereof. For example, a biomedical electrode used to sense the electrical activity of a subject's heart can be configured to convert ionic current into electrical current. By way of further example, a biomedical electrode used to sense the electrical activity of a subject's heart can be configured to convert a potential on the surface of the subject to be processed as an electronic signal in electronics hardware.

In some embodiments, the biomedical sensor system can also be adapted to transmit signals to a receiver. Such signals can include, but are not limited to, one or more of electromagnetic signals and acoustic signals.

By way of example only, some embodiments of the present disclosure are described below with reference to monitoring the electrical activity of a subject's heart, for example, in developing an electrocardiogram (ECG). In such embodiments, the sensors include electrodes. However, it should be understood that the biomedical sensor system of the present disclosure can be used to receive a variety of signals from a subject and/or deliver signals (e.g., electrical currents) to a subject in a variety of diagnostic and/or therapeutic procedures. In addition, because the sensors in the embodiments described below include electrodes, the connectors that connect the sensors to a hub are often described as providing means for electrical communication between the hub and the sensors. However, as described above, it should be understood that the connectors can be adapted to provide a pathway for a variety of types of signals that may be communicated between the sensor(s) and the hub(s). Such communication can include communication from the sensor(s) to the hub(s), as well as from the hub(s) to the sensor(s).

As is generally known in the art, an ECG can be captured via a variety of lead configurations, including, but not limited to 3-lead ECG, 5-lead ECG, and 12-lead ECG, depending on the number of sensing biomedical electrodes placed in contact with the subject. The illustrated embodiments, which are discussed in greater detail below represent a variety of 3-lead and 5-lead ECG configurations, but it should be understood that the same teachings could be applied equally to other lead configurations.

Figure 2:
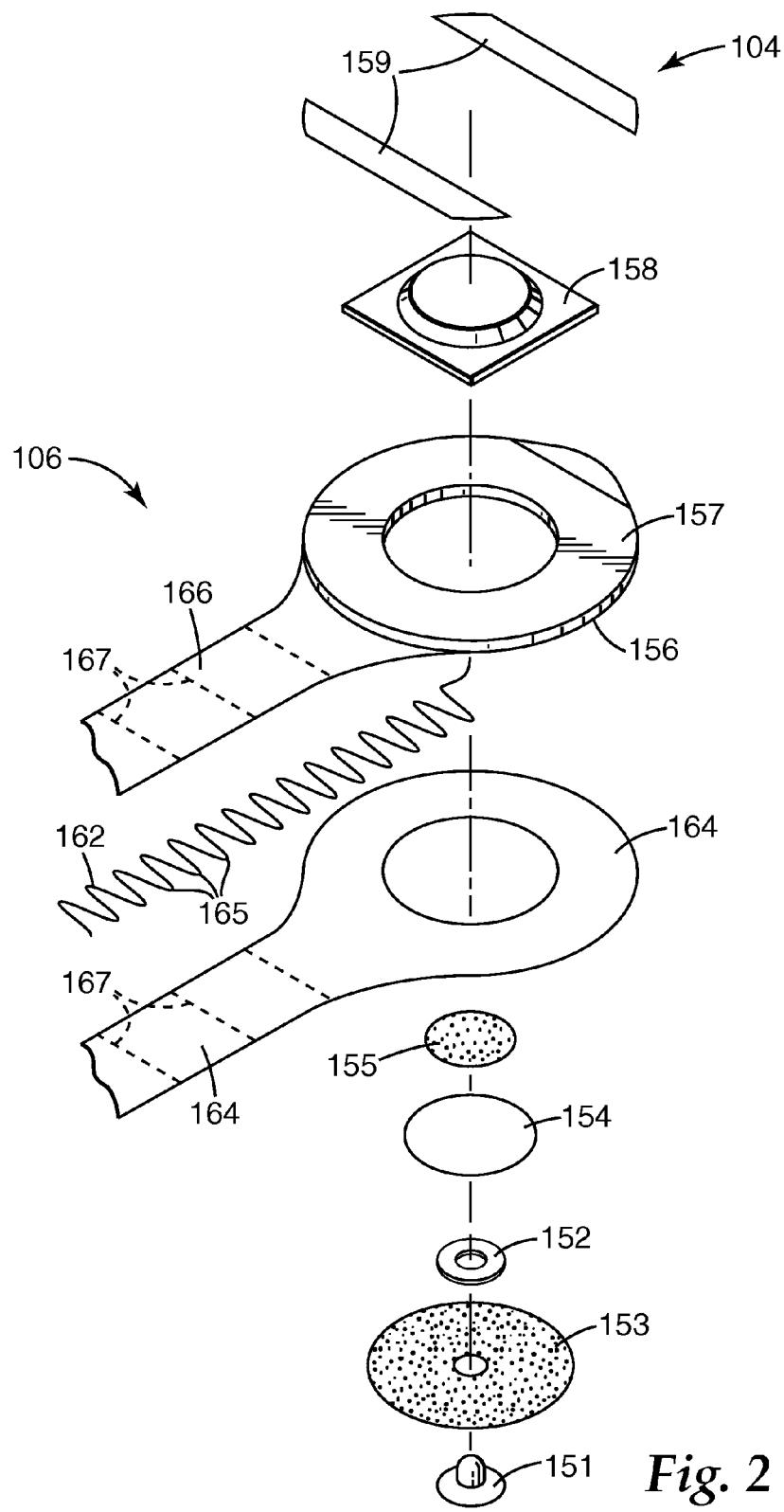
FIG. 2 is a partial perspective exploded bottom view of the biomedical sensor system of FIG. 1.

FIGS. 1 and 2 illustrate a biomedical sensor system 100 according to one embodiment of the present disclosure. FIG. 1 illustrates the biomedical sensor system 100 in a first, unstretched, state, and a second, stretched, state, relative to a subject 50. FIG. 2 illustrates a portion of the biomedical sensor system 100 in the first, unstretched state, with some of the components exemplified in greater detail. The term "subject" is used to generally refer to a person, an animal, or any other matter of biological origin, receiving a diagnostic and/or therapeutic procedure, but is not intended to be limited to subjects of a diseased state, and can instead include normal, healthy subjects. The subject 50 is illustrated as being a human subject; however, it should be understood that the present disclosure is not limited to human subjects.

The biomedical sensor system 100 is configured to produce a 3-lead ECG (i.e., I, right arm—left arm (RA-LA); II, right arm—left leg (RA-LL); and III, left arm—left leg (LA-LL)). As shown in FIG. 1, the biomedical sensor system 100 includes a hub 102, two satellite electrodes 104, and two connectors 106 positioned to couple each satellite electrode 104 to the hub 102. Electrodes 104 sense differential signals with respect to a reference node or signal. Such a reference node or signal can be provided, for example, by one or more of the other electrodes 104 and/or the hub 102. The connectors 106 are also adapted to provide a pathway between the electrodes 104 (or other sensors) and the hub 102 for one or more signals that may be communicated between the electrodes 104 and the hub 102.

The Hub

In some embodiments, the hub 102 provides a single connection site for the biomedical sensor system 100, such that the biomedical sensor system 100 can be connected to downstream computing, signal processing, displaying, and/or archiving equipment via the hub 102. In some embodiments, the hub 102 is a "dummy" hub and serves only to provide a single connection site for the biomedical sensor system 100. The hub 102 can be hard-wired to downstream equipment, or the hub 102 can wirelessly communicate with downstream computing, processing, displaying and/or archiving equipment. The biomedical sensor system 100 illustrated in FIG. 1 includes one hub 102, but it should be understood that in some embodiments, the biomedical sensor system 100 includes multiple hubs 102, and that in such embodiments, each sensor (e.g., electrode 104) can communicate with one or more hubs 102.

In some embodiments, the biomedical sensor system 100 can be used in conjunction with at least a portion of a wireless health monitoring system, such as those described in U.S. Patent Application Publication No. 2007/0279217 (Venkatraman et al.), assigned to HMicro, Inc., Los Altos, Calif., the disclosure of which is incorporate herein by reference. For example, the hub 102 can include at least a portion of the medical signal processor taught by HMicro, and/or the mobile device taught by Venkatraman. In embodiments in which the hub 102 performs at least some of the signal processing, for example, the hub 102 can wirelessly communicate with a receiving device (e.g., a mobile device), which in turn can communicate with a secure server or other computing device via a wireless or wired network.

Figure 13:
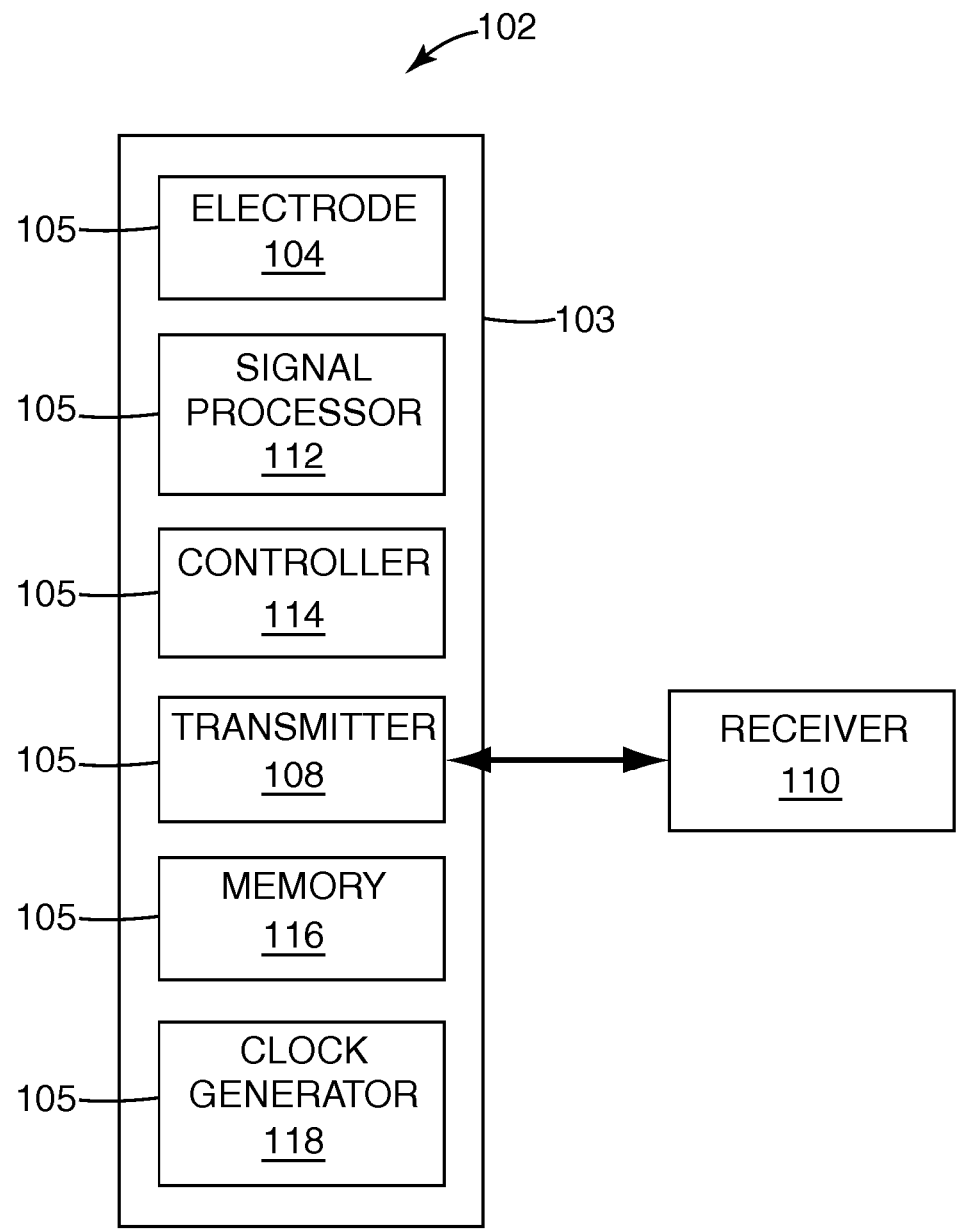
FIG. 13 is a schematic block diagram of a hub according to one embodiment of the present disclosure.

One embodiment of the hub 102 is shown schematically in FIG. 13. As shown in FIG. 13, in some embodiments, the hub 102 can include a variety of electronic processing modules and/or equipment, to perform at least some initial signal processing of the input signal(s) received from one or more electrodes 104. In such embodiments, the hub 102 can include a housing 103 and one or more electronics units 105 that are adapted to be positioned within the housing 103. In some embodiments, the electronic components are packaged together into one electronics unit 105 that can be positioned within the housing 103 prior to use.

In addition, in some embodiments, as shown in FIGS. 1 and 13, the hub 102 can include at least one additional electrode 104 (or other sensor, depending on the type of biomedical sensor system being employed) to receive, respectively, at least one additional electrical signal from the subject or to provide a reference node for the other electrode signals. With continued reference to FIG. 13, in some embodiments, the biomedical sensor system 100 is wireless, and the hub 102 includes a signal processor 112 (such as the medical signal processor taught by Venkatraman et al.) that is adapted to receive one or more signals from one or more of the electrodes 104 (i.e., satellite or hub electrodes 104) and pass the processed signal(s) to a transmitter 108. The transmitter 108 is adapted to translate signals from the electrodes 104 into a signal that can be transmitted (e.g., one or more of an electromagnetic signal, an acoustic signal, and combinations thereof), and wirelessly transmit information relative to the signal(s) from the electrodes 104 to a receiver 110. The receiver 110 can include or be a portion of any necessary downstream computer, signal processor, display and/or archiving equipment, or it can be a separate device that is connected to downstream equipment in a wired or wireless fashion. For example, in some embodiments, the receiver 110 is part of a fixed or mobile device that also includes a signal processor, and which is adapted to communicate with a secure server or other computing device.

In such embodiments, the transmitter 108 can be adapted to send information relative to all of the signals received, or the signal processor 112 can collect and process the one or more signals from the subject to form a combined signal, and the transmitter 108 can be adapted to transmit the combined signal to the receiver 110.

In some embodiments, the hub 102 can further include a controller 114, which can include the signal processor 112 or can be adapted to communicate with the signal processor 112. The controller 114 can provide computing, data processing and/or control functions for the hub 102. The controller 114 can include any of the above signal processor and/or transmitter components, or one or more of the signal processor 112 and the transmitter 108 can include the controller 114, or a portion thereof. In processing the one or more signals from the subject, the signal processor 112 can amplify, filter, and/or digitize the one or more signals, which can then be sent to the controller 114 and/or the transmitter 108. Furthermore, in some embodiments, the transmitter 108 can include at least a portion of the signal processor 112, or vice versa.

Generally, the controller 114 can be a suitable electronic device, such as, for example, a microcontroller, an embedded computer, a field programmable gate array (FPGA), another suitable digital logic device, or a combination thereof. As such, the controller 114 may include both hardware and software components, and is meant to broadly encompass the combination of such components. As should also be apparent to one of ordinary skill in the art, FIG. 13 is a model of one embodiment of the hub 102. Many of the modules shown in FIG. 13 and described herein are capable of being implemented in software executed by a microprocessor or a similar device (e.g., that is part of the hub 102 or that is connected to the hub 102 via a wired or wireless connection) or of being implemented in hardware (e.g., that is part of the hub 102 or that is connected to the hub 102 via a wired or wireless connection) using a variety of components including, for example, application specific integrated circuits ("ASICs").

In some embodiments, the transmitter 108 and/or the signal processor 112 can include a multiplexer to sequentially select signals from the electrodes 104 using any form of multiplexing (e.g., time division multiplexing), an analog-to-digital converter to convert the combined analog signals to digital signals for transmission, a digital signal processor to decimate the digitized signals, and a radio to modulate the digital signals with a carrier signal for transmission to the receiver 110. The receiver 110 can be positioned near the subject or remote from the subject, depending on the type of diagnostic and/or therapeutic procedure being employed. In some embodiments, it may be necessary for the hub 102 to receive information from other equipment (e.g., downstream equipment), and in such embodiments, the transmitter 108 can be a transceiver, or the hub 102 can further include a receiver. The receiver portion of the transceiver, or the separate receiver can be adapted to receive a signal (e.g., an electromagnetic signal) and translate it into a data stream that can be sent to the signal processor 112, the controller 114, and/or the transmitter 108.

Furthermore, as shown in FIG. 13, in some embodiments, the hub 102 can include memory 116 to at least temporarily store information relative to the signals received from the satellite and/or hub electrodes 104. Suitable types of memory can include, but are not limited to, one or more of read-only memory (ROM), random-access memory (RAM), volatile memory (e.g., static random-access memory (SRAM)), non-volatile memory (e.g., FLASH), and combinations thereof. The memory 116 can be adapted to store data relative to the electrode signals prior to transmitting (e.g., via a wired connection or via the transmitter 108), and/or the memory 116 can be adapted to retain data to later be downloaded to a downstream computer, signal processor, display and/or archiving equipment.

As shown in FIG. 13, in some embodiments, the hub 102 can further include a clock generator 118, which can use an externally connected frequency reference device (e.g., a quartz crystal) to generate timing and clock signals for the hub 102.

As mentioned above, the hub 102 includes an additional electrode 104, such that the biomedical sensor system 100 can take up less total surface area on the subject 50, as shown in FIG. 1. In such embodiments, the biomedical sensor system 100 also can be formed of fewer parts and materials, which can reduce the amount of waste produced in manufacturing the biomedical sensor system 100. In such embodiments, the hub 102 and the two satellite electrodes 104 are each adapted to be coupled to a subject (e.g., to a subject's skin).

The Electrode

Each electrode 104 can include one or more biomedical electrode configurations that are generally known to those of ordinary skill in the art. For example, the electrode 104 can include, but is not limited to, one or more of a surface electrode (e.g., disposable), a suction electrode, a floating metal body-surface electrode, a dry electrode, or a combination thereof. In embodiments employing a surface electrode, the surface electrode can include, but is not limited to, bulb-and-plate electrodes (e.g., reusable), pregelled electrodes (e.g., disposable), wet gel electrodes, and combinations thereof. Pregelled electrodes can include an electrolyte that is contained in a cohesive gel that is coupled a current collector. Examples of pregelled electrodes can include, but are not limited to solid gel electrodes (e.g., including a non-adhesive crosslinked hydrogel such as guar gum), sticky gel electrodes (e.g., including an adhesive hydrogel), repositionable electrodes (e.g., including a bicontinuous hydrogel pressure sensitive adhesive), and combinations thereof. Wet gel electrodes can include a dry current collector coupled to a pressure sensitive adhesive-coated substrate, and a wet gel or cream. Prior to application of such electrodes, a volume of wet gel or cream can be applied to the dry current collector to function as the conductive interface on the skin. The wet gel or cream in such embodiments typically has no cohesive properties. Such a wet gel or cream can also be used in bulb-and-plate electrodes. The electrodes 104, including the electrode 104 positioned at the hub 102, can all be of the same type, different types, or a combination thereof.

Non-limiting examples of biomedical electrodes include electrodes disclosed in U.S. Pat. Nos. 4,527,087; 4,539,996; 4,554,924; 4,848,353 (all Engel); U.S. Pat. No. 4,846,185 (Carim); U.S. Pat. No. 4,771,713 (Roberts); U.S. Pat. No. 4,715,382 (Strand); U.S. Pat. No. 5,012,810 (Strand et al.); U.S. Pat. No. 5,133,356 (Bryan et al.), U.S. Pat. No. 3,805, 769 (Sessions); U.S. Pat. No. 3,845,757 (Weyer); U.S. Pat. No. 4,640,289 (Craighead), and U.S. Pat. No. 5,215,087 (Anderson et al.); the disclosures of which are incorporated herein by reference.

Further non-limiting examples of such biomedical electrodes include those marketed by a number of companies (e.g., 3M™ RED DOT™ electrodes, available from 3M Company, St. Paul, Minn.). By way of example only, the electrode 104 is illustrated in FIG. 2 as a snap-type monitoring electrode 104, the components of which are described in greater detail below. However, it should be understood that the electrode 104 illustrated FIG. 2 is illustrated by way of example only, and the present disclosure of a biomedical sensor system should not limited to such electrode constructions.

Additional non-limiting examples of such biomedical electrodes include electrodes that do not contain a gel or electrolyte as an interface between the subject and the current collector. One example of such an electrode is a "capacitive" electrode. In capacitive electrodes, the subject (e.g., the subject's skin) and a metal surface of the sensor function as the plates of a capacitive element.

With reference to the exploded view of the electrode 104 in FIG. 2, a metallic stud 151, (such as stainless steel eyelet No. 304, commercially available from companies such as Eyelets for Industry, Thomaston, Conn.) couples a plastic, metallic plated eyelet 152 (such as an ABS plastic eyelet silver-plated and chlorided, commercially available from Micron Products, Fitchburg, Mass.) through an aperture in a polymeric backing 153 (such as front label stock of printed white polyethylene, commercially available from Prime Graphics, West Chicago, Ill.). The inner surface of the polymeric backing 153 is coated with an adhesive (such as a phenolic-cured smoke crepe natural rubber based adhesive). Contacting the eyelet 152 at the plated surface is a wood pulp scrim 154 (such as an "Airtex 399" scrim, commercially available from James River Corporation, Green Bay, Wis.), loaded with a quantity of a conductive adhesive 155, such as pressure sensitive conductive adhesive (such as the pressure sensitive conductive adhesives described in U.S. Pat. Nos. 4,524,087; 4,539,996; 4,848, 353; and 4,554,924 (all Engel); 5,296,079 (Duan et al.); U.S. Pat. No. 5,385,679 (Uy et al.); U.S. Pat. No. 5,338,490 (Dietz et al.) and U.S. Pat. No. 5,779,632 (Dietz et al)).

The scrim 154 and the conductive adhesive 155 reside in an aperture of an adhesive-coated foam 156. For example, the adhesive-coated foam 156 can include a 0.16 cm thick polyethylene foam coated with either 12 grains of a 91:9 isooctyl acrylate:N-vinyl-2-pyrrolidone copolymer pressure sensitive adhesive or 18 grains of a 94:6 isooctyl acrylate:acrylic acid copolymer tackified with a FORAL™ branded colophony acid rosin, such as "FORAL AX" or "FORAL 85" rosins, commercially available from Hercules Corporation, present in an amount of about 35-40 weight percent of the copolymer solids. The adhesive-coated side of the adhesive-coated foam 156 is covered by a tabbed antifungal liner 157 (such as 83 pound bleached release paper under the brand "Polyslik 5-8004" treated with "Calgon TK-100" brand fungicide, both liner and treatment commercially available from H. P. Smith Company, Chicago, Ill.). The scrim 154 and the conductive adhesive 155 are protected by a cap 158, (such as a 0.25 mm "PETG" polyester film commercially available from Weiss Company, Chicago, Ill.) secured in place by dual strips 159 of adhesive tape (such as 3M™ brand "Type 2185" tape, commercially available from 3M Company, St. Paul, Minn.).

In some embodiments, the means for electrical communication in the electrode 104 can include an electrically conductive tab extending from the periphery of the biomedical electrodes, such as that illustrated and described in U.S. Pat. No. 4,848,353, and/or a conductor member extending through a slit or seam in an insulating backing member, such as that illustrated and described in U.S. Pat. No. 5,012,810. Otherwise, the means for electrical communication can be an eyelet or other snap-type connector such as that disclosed in U.S. Pat. Nos. 4,640,289 and 4,846,185. Further, the means for electrical communication can be a lead wire such as that seen in U.S. Pat. No. 4,771,783.

The Connector

The biomedical sensor system 100 is size-configurable and conformable to the subject 50, at least partially because of the variable-length connectors 106. In some embodiments, the connectors 106 are sized (e.g., in an initial, unstretched, state) to accommodate a relatively small subject but are configurable to accommodate a larger subject. In the embodiment illustrated in FIGS. 1 and 2, the connector 106 is at least partially formed of a viscoelastic material, such that by applying a force to the connector 106 substantially along the length of the connector 106 (e.g., substantially oriented in the first direction $D_1$), the connector 106 can be elongated. A variety of viscoelastic materials can be employed, ranging from viscoelastic materials that are largely elastic and exhibit substantial elastic deformations to viscoelastic materials that exhibit substantial plastic deformations and minimal elastic deformations. One exemplary variable-length electrical connector is described in co-pending, commonly assigned, U.S. Patent Application Ser. No. 61/049,678, entitled "Stretchable Electrical Connector," (Oster et al.), and PCT Patent Application No. PCT/US2009/042010, entitled "Stretchable Conductive Connector," (Oster et al.), the disclosures of which are incorporated herein by reference.

Elongation of the connector 106 can cause the electrode 104 and the hub 102 to be moved farther apart. This size-configurable feature is shown in detail in FIG. 1. Due at least in part to the viscoelastic material of the connector 106, the electrode 104 can be moved from a first position $P_1$ nearer the hub 102 to a second position $P_2$ farther from the hub 102 to accommodate a subject's size, and the electrode 104 can remain at the second position $P_2$ for a desired period of time, for example, throughout the duration of the use of the biomedical sensor system 100. If the second position $P_2$ is not sufficient for accurate placement of the electrode 104 (e.g., given the subject's size), force can again be applied to the connector 106 substantially in the first direction $D_1$, and the electrode 104 can be moved farther away from the hub 102 to a third position (not shown), and so on, until either the plastic properties of the connector 106 are exhausted or the electrode 104 has reached its optimum placement position.

In some embodiments, the length of the connector 106 can be decreased by stretching the connector 106 substantially along its width (e.g., in a direction substantially perpendicular to the first direction $D_1$), such that by extending the width of the connector 106, the length of the connector 106 decreases, and the connector 106 is shortened.

In some embodiments, as shown in the embodiment illustrated in FIG. 1, the electrodes 104 have a fixed angular position but a variable radial position, such that the electrodes 104 do not substantially move angularly about the hub 102 (but may move slightly angularly), but can be moved radially toward or away from the hub 102, due at least in part to the respective variable-length connector 106.

The connectors 106 shown in FIG. 1 are each used to couple one electrode 104 to the hub 102. However, in some embodiments (e.g., in embodiments in which the biomedical sensor system 100 is configured to produce a 12-lead ECG), the biomedical sensor system 100 includes more than one electrode 104 associated with one or more of the connectors 106. For example, in some embodiments, one or more of the connectors 106 can be coupled to a first electrode 104 positioned a first distance along its length, and a second electrode 104 positioned an additional, farther distance along its length, and so on. Alternatively, in some embodiments, a series of connectors 106 can be employed to connect two or more electrodes 104 in series and provide a variable-length between the successive electrodes 104 to accommodate a variety of subject sizes.

The connector 106 mechanically and electrically couples at least one electrode 104 to the hub 102. One connector 106 will be described for clarity and simplicity, but it should be understood that the same explanation applies to all of the connectors 106. Each connector 106 has a variable length, such that the length of the connector 106 can be changed to change the position of the respective electrode 104 and allow the electrode 104 to be positioned a variable distance from the hub 102.

By way of example only, the connector 106 is illustrated in FIG. 2 as comprising a wire as a conductor 162 (e.g., a wire of suitable ductility, such as a copper wire) positioned between a first support member 164, and a second support member 166 to provide a communication pathway (e.g., an electrical communication pathway) between the hub 102 and the electrode 104. In the embodiment illustrated in FIG. 2, the adhesive-coated foam 156 of the electrode 104 is coupled to the bottom surface of the second support member 166. However, it should be understood that, alternatively, the connector 106 can provide portions or components of the electrode construction, such as the adhesive-coated foam 156. For example, in some embodiments employing the electrode 104 illustrated in FIG. 2, the adhesive-coated foam 156 can be integrally formed with a portion of the connector 106 (e.g., a support member 164, 166).

The term "conductor" is used to generally refer to a signal conduction medium that can be used to provide communication from one point to another along the length of the connector 106. For example, in some embodiments, the term "conductor" can be used to generally refer to an electrically conductive material that can be used to provide electrical communication from one point to another along the length of the connector 106. In addition, the term "conductor" can refer to coated or insulated conductors, or exposed, uncoated conductors. Finally, the term "conductor" is not meant to indicate only generally cylindrical structures, but rather can take on any shape or configuration necessary to provide communication in the connector 106. Exemplary electrical conductors can be formed of a variety of materials, including, but not limited to, metal, carbon, graphite, or combinations thereof. In some embodiments, conductive flakes (e.g., formed of metal, carbon, graphite, other suitable conductive materials, or combinations thereof) can function as the conductor 162 and can be provided in a matrix or carrier on one or more of the support members 164, 166, or can be embedded directly into one or more of the support members 164, 166. In some embodiments employing an insulating coating over the conductor, the coating can be made from a relatively electrically conductive material that can be used as a shielding to minimize any interference from unwanted environmental signals.

By way of further example, in some embodiments employing optical signals, the term "conductor" can be used to generally refer to one or more optical fibers. In addition, in some embodiments, the term "conductor" can be used to generally refer to a conductor of another energy modality, such as near infrared light modulation. In some embodiments, the biomedical sensor system 100 can include a variety of the above-described energy modalities, sensors, signals, and/or conductors.

The support members 164, 166 can be formed of a variety of materials capable of changing in length, for example, capable of elongating when a force is applied substantially in the first direction $D_1$. Particular utility has been discovered when the support members 164, 166 are formed of a viscoelastic material, such that the connector 106 may exhibit at least some elastic properties but when sufficient force is applied and/or the connector 106 is elongated past a certain point, the connector 106 does not exhibit immediate elastic recovery. In some embodiments, such viscoelastic properties can allow an electrode 104 to be positioned at the desired location on the subject 50, without the electrode 104 pulling on the skin due to substantial elastic spring forces associated with the connector 106. On the contrary, at least some plastic deformation can occur as force is applied to the connector 106 to elongate the connector 106, allowing the electrode 104 to remain in a second position $P_2$ for a desired period of time. Such viscoelastic materials are embodied, for example, in 3M™ COMMAND™ adhesive articles, particularly, in the backings of such articles, commercially available from 3M Company, St. Paul, Minn. 3M™ COMMAND™ backings are examples of multilayer laminates of individually viscoelastic materials that exhibit necking at low yield stresses and have high elongations at break. Such backings can be useful as one or more of the support members 164, 166. The support members 164, 166 can be coupled together using, for example, any of the pressure sensitive adhesives described herein. One example of a multilayer laminate that can be employed in one or more of the support members 164, 166 includes a linear low density polyethylene (LLDPE)/polyethylene (PE) foam/LLDPE trilayer laminate.

In some embodiments, at least a portion of the connector 106, such as one or more of the support members 164, 166 can be formed of a material whose dimensions change in response to heating or cooling. For example, in some embodiments, it may be desirable to reduce the length of the connector 106 after the appropriate length has been determined. By way of example only, at least a portion of the connector 106, such as one or more of the support members 164, 166 can be formed of a material that exhibits shrinkage, for example, upon warming or heating (e.g., with a hot air gun), such that the connector 106 can be shortened on demand.

In some embodiments, the adhesive that couples the electrode 104 (and/or the hub 102) to the subject (e.g., the adhesive of the adhesive-coated foam 156) can include a stretch release adhesive, such as those described in U.S. Pat. Nos. 6,527,900, 5,516,581, 5,672,402, and 5,989,708 (Kreckel et al.); U.S. Patent Application Publication No. 2001/0019764 (Bries, et al.); and U.S. Pat. Nos. 6,231,962 and 6,403,206 (Bries et al.), each of which is commonly owned by the Assignee of the present application, and is incorporated herein by reference. In such embodiments, the adhesive can be coupled (e.g., directly or indirectly) to at least a portion of the connector 106, such as one or more of the support members 164, 166, which in turn can function as the "backing" to the stretch release adhesive. As a result, the connector 106 (e.g., one or more of the support members 164, 166) can include one or more stretchable layers that can be stretched to a point that causes debonding of the adhesive.

In such embodiments, the connector 106 can be elongated for proper placement of each satellite electrode 104 (and to accommodate proper placement of the electrode 104 at the hub 102), and when it is time to remove the electrodes from the subject (e.g., the subject's skin), the connectors 106 can be stretched again until debonding of the adhesives occur, and the hub 102 and the satellite electrodes 104 are removed from the skin. In such embodiments, the adhesive can be designed such that the initial elongation of the connector 106 for placement of the electrode 104 is not sufficient to inhibit the bonding properties of the adhesive.

Suitable materials for any of the stretchable layers of the connector 106 can include any materials which are stretchable without rupture by at least 50 percent elongation at break and which have sufficient tensile strength so as not to rupture before debonding of the adhesive. Such stretchable materials may be either elastically deformable or plastically deformable, provided sufficient stretching is possible to cause adhesive debonding of both adhesive surfaces for stretch removal.

Suitable plastic backing materials are disclosed in the above listed U.S. patents to Kreckel et al. and Bries et al. Representative examples of materials suitable for either a polymeric foam or solid polymeric film layer in the connector 106 of the type utilizing a plastic backing include polyolefins, such as polyethylene, including high density polyethylene, low density polyethylene, linear low density polyethylene, and linear ultra low density polyethylene, polypropylene, and polybutylenes; vinyl copolymers, such as polyvinyl chlorides, both plasticized and unplasticized, and polyvinyl acetates; olefinic copolymers, such as ethylene/methacrylate copolymers, ethylene/vinyl acetate copolymers, acrylonitrile-butadiene-styrene copolymers, and ethylene/propylene copolymers; acrylic polymers and copolymers; polyurethanes; and combinations of the foregoing. Mixtures or blends of any plastic or plastic and elastomeric materials such as polypropylene/polyethylene, polyurethane/polyolefin, polyurethane/polycarbonate, polyurethane/polyester, can also be used.

Polymeric foam layers for use in the plastic backing of the connector 106 can include a density of about 2 to about 30 pounds per cubic foot (about 32 to about 481 kg/m$^3$), particularly in constructions where the foam is to be stretched to effect debonding of the adhesive. Particular utility has been found with polyolefin foams, including those available under the trade designations "VOLEXTRA" and "VOLARA," commercially available from Voltek, Division of Sekisui America Corporation, Lawrence, Mass.

Elastomeric materials suitable as materials for stretch release constructions of the connector 106 include styrene-butadiene copolymer, polychloroprene (neoprene), nitrile rubber, butyl rubber, polysulfide rubber, cis-i, 4-polyisoprene, ethylene-propylene terpolymers (EPDM rubber), silicone rubber, polyurethane rubber, polyisobutylene, natural rubber, acrylate rubber, thermoplastic rubbers such as styrene butadiene block copolymer and styrene-isoprene-styrene block copolymer and TPO rubber materials.

Solid polymeric film backings can include polyethylene and polypropylene films, such as linear low density and ultra low density polyethylene films, such as a polyethylene film available under the trade designation "MAXILENE 200" from Consolidated Thermoplastics Company, Schaumburg, Ill.

The connector 106 (e.g., one or more of the support members 164, 166) may vary in overall thickness so long as it possesses sufficient integrity to be processable and provides the desired performance with respect to stretching properties for debonding the adhesive from the skin. The specific overall thickness selected for the connector 106 can depend upon the physical properties of the polymeric foam layer(s) and any solid polymeric film layer that make up the connector 106. Where only one polymeric film or foam layer of a multi-layer connector 106 is intended to be stretched to effect debonding, that layer should exhibit sufficient physical properties and be of a sufficient thickness to achieve that objective.

A plastic polymeric film layer can be about 0.4 to 10 mils (0.01 mm to 0.25 mm) in thickness, and particularly, can be about 0.4 to 6 mils (0.01 mm to 0.15 mm) in thickness.

The above-listed connector materials are described as being useful in embodiments employing a stretch release adhesive in the electrodes 104. However, it should be understood that the connectors 106 can include any of the above-listed materials even in embodiments that do not employ a stretch release electrode adhesive. That is, the above-listed materials can provide the stretchable, variable-length properties to the connectors 106 for placement of the electrodes 104, even in embodiments that will not require the stretchable properties for removal of the electrodes 104.

The adhesive of the adhesive layer(s) of the electrodes 104 can comprise any pressure-sensitive adhesive, particularly any pressure sensitive adhesive suitable for adhesion to the skin. In some embodiments, the adhesion properties generally range from about 4 N/dm to about 200 N/dm, in some embodiments, from about 25 N/dm to about 100 N/dm, at a peel angle of 180°, measured according to PSTC-1 and PSTC-3 and ASTM D 903-83 at a peel rate of 12.7 cm/min. Adhesives having higher peel adhesion levels usually require connectors 106 having a higher tensile strength.

Suitable pressure-sensitive adhesives include tackified rubber adhesives, such as natural rubber; olefins; silicones, such as silicone polyureas; synthetic rubber adhesives such as polyisoprene, polybutadiene, and styrene-isoprene-styrene, styrene-ethylene-butylene-styrene and styrene-butadiene-styrene block copolymers, and other synthetic elastomers; and tackified or untackified acrylic adhesives such as copolymers of isooctylacrylate and acrylic acid, which can be polymerized by radiation, solution, suspension, or emulsion techniques.

In some embodiments, the thickness of each adhesive layer can range from about 0.6 mils to about 40 mils (about 0.015 mm to about 1.0 mm), and in some embodiments, from about 1 mils to about 16 mils (about 0.025 mm to about 0.41 mm).

Adhesives for adhering one polymeric foam layer to either another polymeric foam layer or a solid polymeric film layer include those pressure-sensitive adhesive compositions described above. In some embodiments, the adhesive layer for adjoining one polymeric layer of the connector 106 (e.g., one support member 164 or 166) to another will be about 1 to 10 mils (about 0.025 to 0.25 mm) in thickness. Other methods of adhering the polymeric layers of the backing (i.e., the support members 164 and 166) to one another include such conventional methods as co-extrusion or heat welding.

The adhesive of the electrodes 104 (including the adhesive on the hub 102) can be produced by any conventional method for preparing pressure-sensitive adhesive tapes. For example, the adhesive can either be directly coated onto a backing (e.g., a support member 164 or 166 of the connector 106), or it can be formed as a separate layer and then later laminated to the backing In some embodiments, the viscoelastic material employed in the connector 106 can allow percent elongations of at least 200%, in some embodiments, at least 300%, and in some embodiments, at least 600%. For example, Table 1 lists the mechanical properties of metallocene catalyzed linear low density polyethylene (LLDPE) and Ziegler Natta catalyzed LLDPE at various processing conditions. Such linear low density polyethylenes would be suitable for use in one or more of the support members 164, 166 of the connector 106. The information contained in Table 1 was obtained from Ruksakulpiwat, "Comparative study and structure and properties of Ziegler-Natta and metallocene based linear low density polyethylene in injection moldings," as published in ANTEC-2001, Conference Proceedings, Volume-1, CRC Press, pp 582-586.

TABLE 1

Mechanical properties of metallocene catalyzed LLDPE (mLLDPE5100) and Ziegler Natta catalyzed LLDPE (ZNLLDPE2045) at various processing conditions

| Processing condition | Tensile Strength (MPa) | | Yield Strength (MPa) | | % Elongation at break | |
|---|---|---|---|---|---|---|
| | mLLDPE5100 | ZNLLDPE2045 | mLLDPE5100 | ZNLLDPE2045 | mLLDPE5100 | ZNLLDPE2045 |
| 1 | 14.49 | 13.29 | 13.28 | 12.33 | 655.2 | 726.2 |
| 2 | 1368 | 13.24 | 12.99 | 12.92 | 657.2 | 831.8 |
| 3 | 13.35 | 12.36 | 12.45 | 12.39 | 640.3 | 769.0 |
| 4 | 13.76 | 13.21 | 13.05 | 12.51 | 662.1 | 755.2 |
| 5 | 13.47 | 13.36 | 12.76 | 12.75 | 652.3 | 777.0 |
| 6 | 13.41 | 13.28 | 12.71 | 12.65 | 654.8 | 759.9 |
| 7 | 12.91 | 12.99 | 12.31 | 12.30 | 665.5 | 760.4 |

In addition, the support members 164, 166 can provide insulation (e.g., electrical insulation) to the conductor 162 in addition to, or in lieu of, an insulating coating or sheath that may encapsulate the conductor 162. As a result, particular utility can be found when support members 164, 166 are employed that not only have a variable length and have the ability to be elongated or shortened, but also which provide insulation to the means for providing communication along the connector 106.

Figure 5:
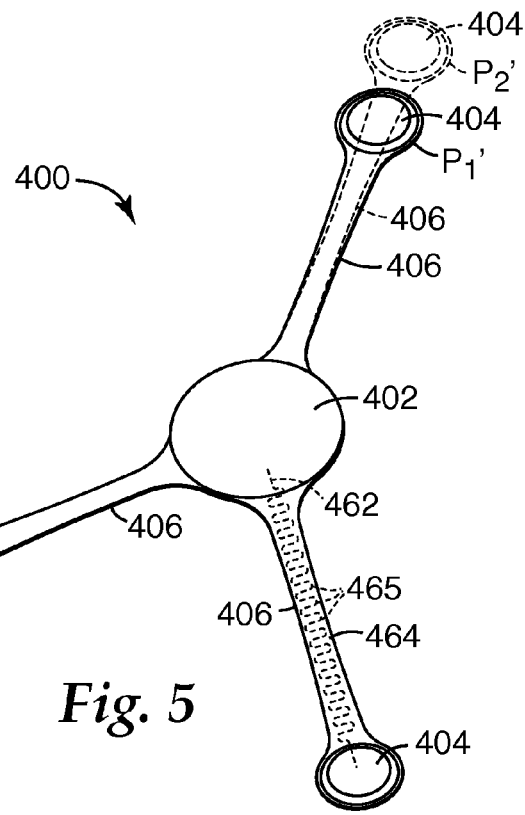
FIG. 5 is a perspective view of a biomedical sensor system according to another embodiment of the present disclosure.

In the embodiment illustrated in FIG. 2, the conductor 162 is positioned between the first and second support members 164 and 166; however, it should be understood that the conductor 162 can instead be positioned within a single support member (e.g., embedded in a support member, as shown in FIG. 5 and described below). By way of example, the conductor 162 includes a plurality of bends 165 to allow the conductor 162 to maintain electrical communication between the electrode 104 and the hub 102 when the connector 106 is elongated or shortened. The number of bends 165 along the length of the connector 106 and the radius of curvature of each bend 165 can be determined to accommodate the desired extensibility or contractibility of the connector 106, and the material makeup of the connector 106 (e.g., the material makeup of the one or more support members 164, 166).

In embodiments of the biomedical sensor system 100 that employ a different type of sensor and a different type of communication between the sensor and the hub 102, the communication pathway can also include a plurality of bends so as to accommodate the variable-length connector 106, and such embodiments need not only apply to electrical communication.

The conductor 162 shown in FIG. 2 is positioned such that it will couple to the metallic stud 151 of the electrode 104.

However, it should be understood that the end of the conductor 162 that contacts any conductive element(s) of the electrode 104 can be adapted to couple to such conductive elements in a variety of ways, including, but not limited to, clamps, snap-fit connectors (e.g., the distal end of the conductor 162 can be coupled to a snap-fit connector that will couple to the metallic stud 151 via a snap-fit-type engagement), other suitable coupling means, and combinations thereof The conductor 162 is shown as a wire by way of example only. However, additionally or alternatively, in some embodiments, communication between the electrode 104 and the hub 102 can be provided by a variety of other conductive materials. For example, electrical communication can be provided by a variety of electrically conductive materials, including, but not limited to, printed metal inks (e.g., conductive polymer thick film inks, commercially available from Ercon Inc., Wareham, Mass.); conductive thick film laminates (e.g., die cut silver, such as a die cut silver backing from 3M™ RED DOT™ electrodes, available from 3M Company, St. Paul, Minn.); conductive polymers (e.g., Ormecon polyaniline, commercially available from Ormecon GMBH, Ammersbek, Germany; PEDOT (polyethylendioxythiophene), commercially available from Bayer, Leverkusen, Germany); other suitable electrically conductive materials; or a combination thereof. Other suitable means for providing conductivity along the length of the connector 106 to provide electrical communication between the electrode(s) 104 and the hub 102 can be understood by one of skill in the art and can be employed without departing from the spirit and scope of the present disclosure.

In some embodiments, the biomedical sensor system 100, or a portion thereof, such as the electrodes 104 and the connectors 106, can be disposable. In some embodiments, the hub 102 can also be disposable. Such disposable embodiments can be inexpensive and can be made from high-speed, facile, and inexpensive fabrication techniques. In addition, such disposable embodiments can be lightweight, can improve subject comfort, can reduce wiring complexity, can reduce overall costs, can reduce healthcare-associated infections, and can lead to improved patient outcomes. In some embodiments, disposable connectors 106, or disposable electrode/hub-connector assemblies (e.g., in which one or more electrodes 104 and/or hubs 102 are coupled to one or more connectors 106 to form a disposable assembly) can be formed from any of the 3M™ COMMAND™ adhesive articles materials and constructions described above. For example, in some embodiments, disposable connectors 106 or disposable electrode/hub-connector assemblies can be formed from a multilayer laminate comprising a first 3M™ COMMAND™ backing (e.g., with a corresponding 3M™ COMMAND™ adhesive), a conductive thick film laminate (such as the die cut silver described above), and a second 3M™ COMMAND™ backing. Such a construction would also provide radiotransparency to minimize or eliminate any disruptions when imaging the subject. In such embodiments, the conductive thick film laminate can include the bends 165 shown in FIG. 2, and one or more of the support members 164, 166 can include one or more slits or weakened regions 167 to further accommodate varying the length of the connector 106. For example, in some embodiments, the one or more slits or weakened regions 167 can correspond with every bend 165, every other bend 165, every fourth bend 165, or the like.

One potential advantage of employing a wire as the conductor 162 over other means of providing electrical communication is that the wire will not exhibit a change in resistance as the length of the connector 106 is changed because the cross-sectional area of the wire will not change as the length of the connector 106 is changed, but rather the radius of curvature of the bends 165 of the wire will change, and the distance between adjacent segments of the wire will change.

In some embodiments employing a wire as the conductor 162, the wire can include a magnet wire (e.g., formed of one or more of copper, tin, carbon/graphite, other suitable wire materials, or a combination thereof) that is coated with a polymer (e.g., such as polyethylene, polyphenylene ether, other suitable polymers, or a combination thereof). Such embodiments of the conductor 162 can provide additional advantages, including, but not limited to, water resistance and electromagnetic shielding (e.g., in x-ray applications).

In addition, in some embodiments, the connector 106 can also be adapted to be coupled to the subject 50 (e.g., to the subject's skin). For example, in some embodiments, the connector 106 can include an adhesive, such as an adhesive that would be employed in the electrode 104, such that, for example, when the connector 106 has been extended from a first unstretched state to a second stretched state (i.e., the respective electrode 104 has moved from the first position $P_1$ to the second position $P_2$), the connector 106 can be coupled to the subject 50. In such embodiments, at least a portion of the connector's adhesive can include a stretch release adhesive, such as those described above.

Figure 3:
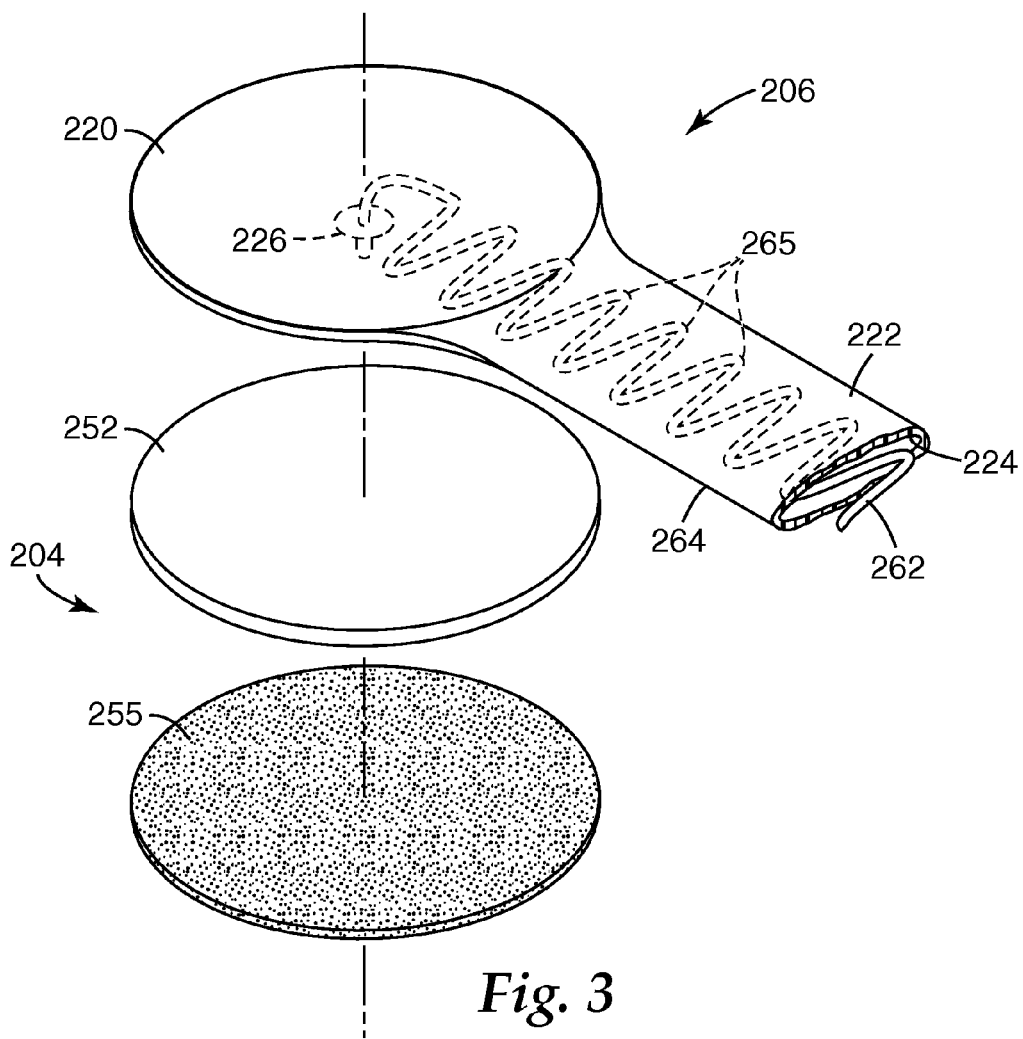
FIG. 3 is a perspective exploded top view of an electrode and connector according to one embodiment of the present disclosure.

FIG. 3 illustrates an electrode 204 and a connector 206 according to another embodiment of the present disclosure, wherein like numerals represent like elements. The electrode 204 and the connector 206 share many of the same elements and features described above with reference to the electrode(s) 104 and the connector(s) 106 of FIGS. 1-2. Reference is made to the description above accompanying FIGS. 1-2 for a more complete description of the features and elements (and alternatives to such features and elements) of the electrode 204 and the connector 206.

As shown in FIG. 3, the electrode 204 includes a conductive adhesive 255 (e.g., an ionically conductive adhesive), such as a pressure sensitive conductive adhesive (such as those mentioned above). The bottom portion of the conductive adhesive 255 shown in FIG. 3 is coupled to a subject in use. The electrode 204 further includes a conductor 252 (e.g., a disk-shaped conductor 252, as shown in FIG. 3, but it should be understood that other shapes are possible), which takes the place of the metallic stud 151 and/or the metallic plated eyelet 152 of the electrode 104 described above with reference to FIG. 2. In some embodiments, the conductor 252 can include silver, a silver ink, and/or a silver-chloride ink (e.g., electrically-conductive polymer thick film inks, commercially available from Ercon Inc., Wareham, Mass.). When the electrode 204 is assembled, the conductor 252 is positioned in electrical communication with the conductive adhesive 255 to provide electrical communication between the conductive adhesive 255 of the electrode 204 and the connector 206.

The connector 206 includes a support member 264 and a conductor 262 positioned within an interior 224 of the support member 264 to provide electrical communication between the electrode 204 and a hub (e.g., the hub 102 of the biomedical sensor system 100 shown in FIG. 1). The support member 264 includes a distal portion 220 and a tubular portion 222 positioned intermediately of the distal portion 220 and a hub. The distal portion 220 and the tubular portion 222 of the connector 206 together define the interior 224. The distal portion 220 is shaped and sized to be coupled to the conductor 252 of the electrode 204 with minimal surface area of the conductor 252 wasted or unused. Thus, the distal portion 220 of the embodiment illustrated in FIG. 3 has a substantially hollow circular shape, but it should be understood that other shapes can be employed. By way of example only, the tubular portion 222 of the connector 206 is illustrated as being at least partially flattened. Such a flattened structure can enhance conformability of the connector 206 to a subject.

The support member 264 can be formed of the same materials described above with respect to the support members 164, 166 of FIG. 2. In some embodiments, the support member 264 is formed of a viscoelastic material to allow the electrode 204 coupled to one end of the connector 206 (e.g., the distal portion 220 at the distal end of the connector 206) to be moved from a first position nearer a hub to a second position farther from the hub to accommodate a subject's size, and the electrode 204 can remain at the second position for a desired period of time.

Similar to the conductor 162 described above, the conductor 262 includes a plurality of bends 265 to allow the conductor 262 to maintain electrical communication between the electrode 204 and a hub when the connector 206 is elongated or shortened.

The number of bends 265 along the length of the connector 206 and the radius of curvature of each bend 265 can be determined to accommodate the desired extensibility or contractibility of the connector 206, and the material makeup of the connector 206 (e.g., the material makeup of the support member 264).

The conductor 262 is shown in FIG. 3 as extending outwardly of the distal portion 220 via an aperture 226 defined in the distal portion 220. Particularly, the conductor 262 is shown in FIG. 3 as extending downwardly out of the connector 206 and configured to electrically communicate with the conductor 252 of the electrode 204 when the electrode 204 and the connector 206 are assembled. In some embodiments, the conductor 262 can include a braided conductor, and the end of the braided conductor can be stripped, with the individual conductors splayed out to provide multiple points of contact (e.g., a braided wire can be used to provide multiple points of electrical contact). In some embodiments, the conductor 262 can include a variety of coupling means, such as a snap-fit connector, adapted to couple with a mating connector on the conductor 252 of the electrode 204. In some embodiments, the conductive adhesive 255 can be put into contact over a portion of the conductor 262, which can be selected to form a nonpolarizable interface between the conductive adhesive 255 (e.g., which can include water and dissolved salt) and the conductor 262 (e.g., at least a portion of which can be made from silver-silver chloride). Such embodiments can eliminate the conductor 252.

The electrode 204 and the connector 206 can be employed in any of the biomedical sensor systems described herein. In addition, the electrode 204 and the connector 206 can be used independently of one another and are illustrated in FIG. 3 together by way of example only. Furthermore, one of ordinary skill in the art should understand that the electrode 204 and the connector 206 can be used in combination with any of the other components described herein with respect to other embodiments.

Figure 4:
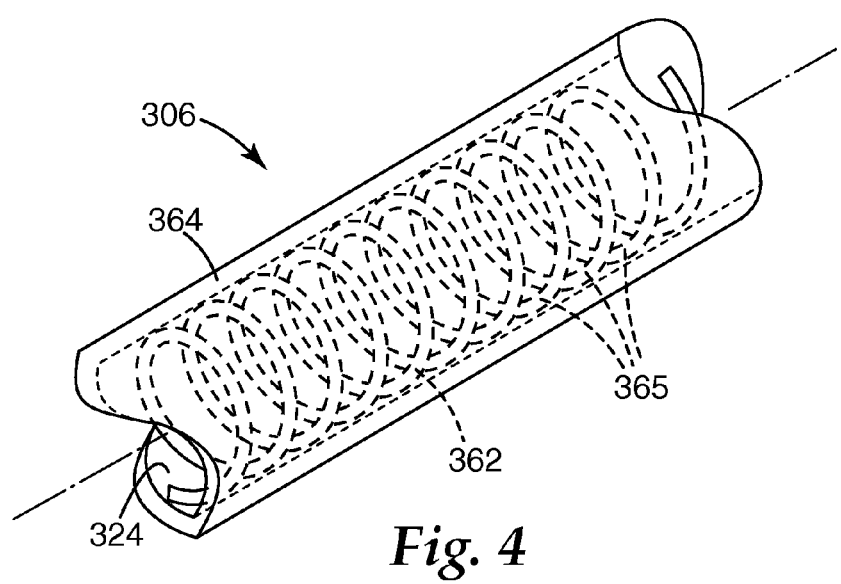
FIG. 4 is a partial perspective view of a connector according to one embodiment of the present disclosure.

FIG. 4 illustrates a connector 306 according to another embodiment of the present disclosure, wherein like numerals represent like elements. The connector 306 shares many of the same elements and features described above with reference to the connector(s) 106 and 206 of FIGS. 1-3. Reference is made to the description above accompanying FIGS. 1-3 for a more complete description of the features and elements (and alternatives to such features and elements) of the connector 306.

As shown in FIG. 4, the connector 306 includes a tubular-shaped support member 364 that defines an interior 324. A conductor 362 can be positioned within the interior 324 of the support member 364 to provide electrical communication between an electrode (e.g., the electrode 104 of the biomedical sensor system 100 shown in FIGS. 1 and 2) and a hub (e.g., the hub 102 of the biomedical sensor system 100 shown in FIGS. 1 and 2).

The support member 364 can be formed of the same materials described above with respect to the support members 164, 166 of FIG. 2 to provide the same variable-length property to the connector 306.

The conductor 362 includes a helical or spiral configuration comprising a plurality of loops or bends 365 to allow the conductor 362 to maintain communication between an electrode and a hub when the connector 306 is elongated or shortened. The number of bends 365 along the length of the connector 306 and the distance between adjacent bends 365 can be determined to accommodate the desired extensibility or contractibility of the connector 306, and the material makeup of the connector 306 (e.g., the material makeup of the support member 364).

In some embodiments, the helical configuration of the conductor 362 can provide more conductor 362 per unit length of the connector 306 than other embodiments, which can accommodate a support member material having greater percent elongation, such that electrical communication is maintained even at high levels of elongation. For example, in some embodiments, the helical conductor 362 can accommodate support members 364 having higher peak strains or percent elongations (e.g., at least about 500%, at least about 600%, etc.).

In some embodiments, the conductor 362 can be molded with the support member 364. For example, the support member 364 can be extruded over the prekinked or precoiled conductor 362 (e.g., following a similar method to extruding processes employed with respect to linear conductor, such as wires), or the conductor 362 can held in place by a pressure sensitive adhesive that is coated on the inner surface of the interior 324 of the support member 364.

In some embodiments, the connector 306 can include a core (e.g., formed of the same material as the support member 364), over which the conductor 362 can be wound. The support member 364 can then be extruded over the conductor 362 and core. In some embodiments, the support member 364 includes the core. By way of example only, a shielded stretchable connector 306 can be formed by co-extruding a three layer system of (1) a support member material (e.g., linear low density polyethylene (LLDPE)), (2) a carbon-filled support member material (e.g., carbon-filled LLDPE), and (3) a support member material (e.g., LLDPE) over the conductor 362.

The connector 306 can be employed in any of the biomedical sensor systems described herein. In addition, one of ordinary skill in the art should understand that the connector 306 can be used in combination with any of the other components described herein with respect to other embodiments.

While the connectors 106, 206, and 306 are illustrated separately in FIGS. 2, 3 and 4, respectively, it should be understood that one or more of the connectors 106, 206, 306 can be used in combination. For example, in some embodiments, one or more of the connectors 106, 206, 306 can be used in parallel in one biomedical sensor system, or in series to provide electrical communication from a hub to one or more electrodes.

FIG. 5 illustrates a biomedical sensor system 400 according to another embodiment of the present disclosure, wherein like numerals represent like elements. The biomedical sensor system 400 shares many of the same elements and features described above with reference to the illustrated embodiment of FIGS. 1-2. Accordingly, elements and features corresponding to elements and features in the illustrated embodiment of FIGS. 1-2 are provided with the same reference numerals in the 400 series. Reference is made to the description above accompanying FIGS. 1-2 for a more complete description of the features and elements (and alternatives to such features and elements) of the embodiment illustrated in FIG. 5.

Similar to the biomedical sensor system 100 illustrated in FIGS. 1-2, the biomedical sensor system 400 is configured to produce a 3-lead ECG. As shown in FIG. 5, the biomedical sensor system 400 includes a hub 402, three satellite electrodes 404, and three connectors 406 positioned to couple each satellite electrode 404 to the hub 402. Each connector 406 is also adapted to provide a pathway for communication of a signal between the electrode 104 and the hub 102 (e.g., an electrical signal).

Unlike the biomedical sensor system 100 shown in FIGS. 1 and 2, the hub 402 of the biomedical sensor system 400 does not include an additional electrode. As a result, in order to be configured for a 3-lead ECG, the biomedical sensor system 400 includes three satellite electrodes 404. The hub 402 can be coupled to a subject, for example, by employing a similar adhesive to that employed by the satellite electrodes 404 (e.g., a pressure-sensitive adhesive), or the hub 402 can be positioned near the subject, without being coupled to the subject. Whether the hub 402 is coupled to the subject, the hub 402 can remain near the subject in use to allow the biomedical sensor system 400 to maintain a low profile and to conform to the subject (e.g., to conform to a patient's body).

One of the satellite electrodes 404 is shown in a first position $P_1'$ nearer the hub 402 and a second position $P_2'$ farther away from the hub 402. As demonstrated by the first and second positions $P_1'$, $P_2'$ of the electrode 404, the electrode 404 can be moved substantially radially toward and away from the hub 402 due at least in part to elongation of the respective connector 406. Similar to the connector 106 described above, the connector 406 is adapted to allow an electrode 404 to be moved radially with respect to the hub 402 without allowing substantial angular movement with respect to the hub 402.

Furthermore, as shown in one of the connectors 406 illustrated in FIG. 5, in some embodiments, the connector 406 can include a conductor 462 comprising a plurality of bends 465 that is embedded in a support member 464, such that the conductor 462 provides electrical communication between the respective electrode 404 and the hub 402 while also having the capacity to accommodate an elongation, or shortening, of the connector 406/support member 464. Alternatively, the connector 406 can take on the form of any of the previously-described connectors 106, 206, 306, or another suitable form that provides a variable length and electrical communication between one or more electrodes 404 and the hub 402.

The conductor 462 can be embedded in the support member 464 in a variety of manners. For example, the conductor 462 can be molded, extruded, heat sealed, or otherwise formed with the support member 464.

Figure 6:
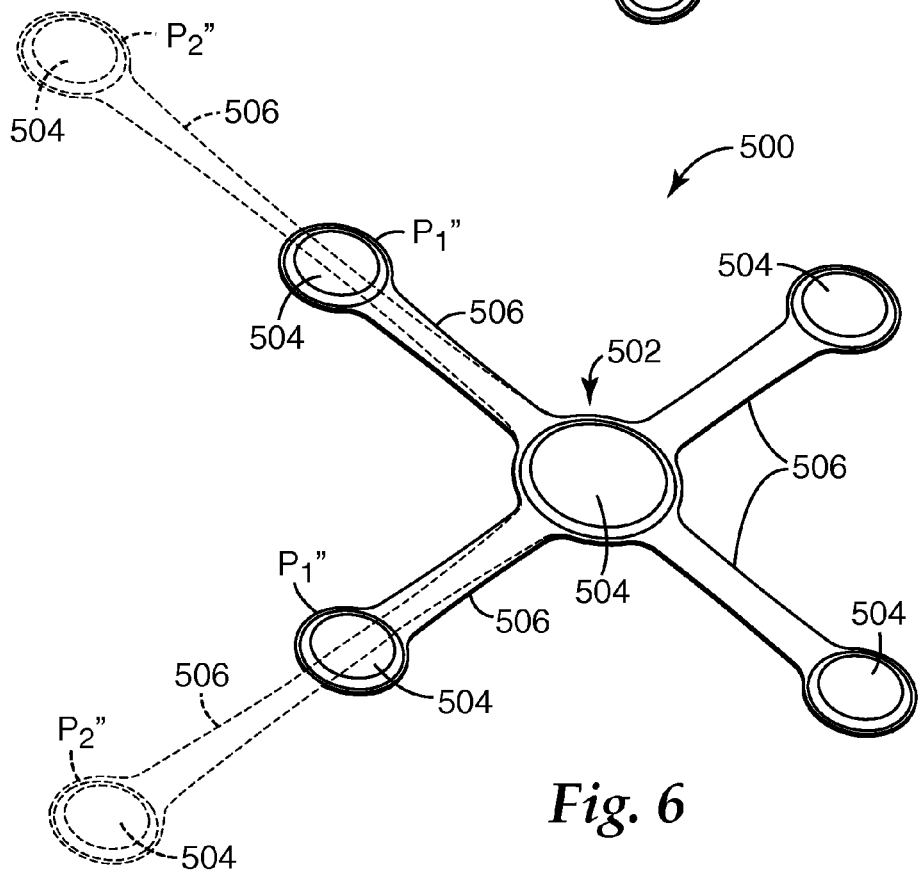
FIG. 6 is a perspective view of a biomedical sensor system according to another embodiment of the present disclosure.

FIG. 6 illustrates a biomedical sensor system 500 according to another embodiment of the present disclosure, wherein like numerals represent like elements. The biomedical sensor system 500 shares many of the same elements and features described above with reference to the illustrated embodiment of FIGS. 1-2. Accordingly, elements and features corresponding to elements and features in the illustrated embodiment of FIGS. 1-2 are provided with the same reference numerals in the 500 series. Reference is made to the description above accompanying FIGS. 1-2 for a more complete description of the features and elements (and alternatives to such features and elements) of the embodiment illustrated in FIG. 6.

The biomedical sensor system 500 is configured to produce a 5-lead ECG. As shown in FIG. 6, the biomedical sensor system 500 includes a hub 502, four satellite electrodes 504, and four connectors 506 positioned to mechanically and electrically couple each satellite electrode 504 to the hub 502. Similar to the biomedical sensor system 100 illustrated in FIGS. 1 and 2, the hub 502 includes an electrode 504. All of the electrodes 504 can be of the same or a different type, or a combination thereof. Each of the hub 502 and the four satellite electrodes 504 can be adapted to be coupled to a subject's skin, for example, by employing an appropriate pressure-sensitive adhesive.

Two of the satellite electrodes 504 are shown in a first position $P_1''$ nearer the hub 502 and a second position $P_2''$ farther away from the hub 502. As demonstrated by the first and second positions $P_1''$, $P_2''$ of the electrode 504, the electrode 504 can be moved substantially radially toward and away from the hub 502 due at least in part to elongation of the respective connector 506. Similar to the connector 106 described above, the connector 506 is adapted to allow an electrode 504 to be moved radially with respect to the hub 402 without allowing substantial angular movement with respect to the hub 502. The connector 506 can take on the form of any of the previously-described connectors 106, 206, 306, 406 or another suitable form that provides a variable length and a communication pathway between one or more electrodes 504 and the hub 502.

Figure 7:
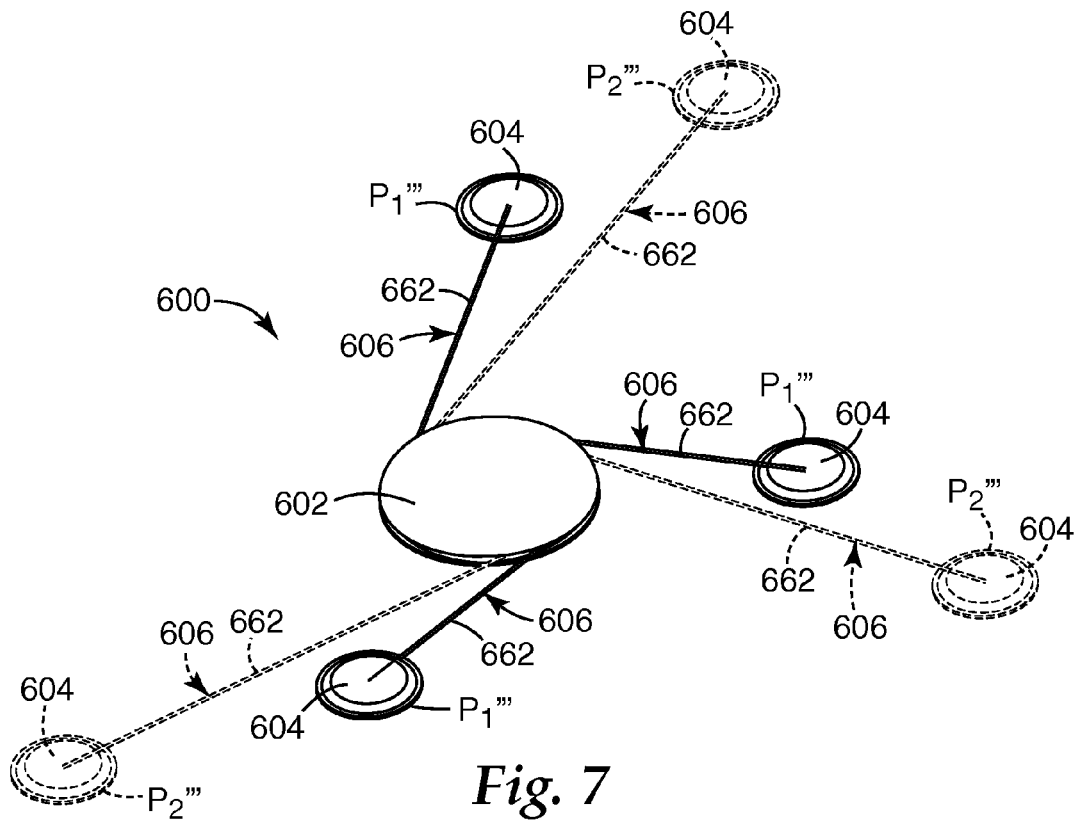
FIG. 7 is a perspective view of a biomedical sensor system according to another embodiment of the present disclosure.

FIG. 7 illustrates a biomedical sensor system 600 according to another embodiment of the present disclosure, wherein like numerals represent like elements. The biomedical sensor system 600 shares many of the same elements and features described above with reference to the illustrated embodiment of FIGS. 1-2. Accordingly, elements and features corresponding to elements and features in the illustrated embodiment of FIGS. 1-2 are provided with the same reference numerals in the 600 series. Reference is made to the description above accompanying FIGS. 1-2 for a more complete description of the features and elements (and alternatives to such features and elements) of the embodiment illustrated in FIG. 7.

Similar to the biomedical sensor system 400 illustrated in FIG. 5, the biomedical sensor system 600 is configured to produce a 3-lead ECG. As shown in FIG. 7, the biomedical sensor system 600 includes a hub 602, three satellite electrodes 604, and three connectors 606 positioned to mechanically and electrically couple each satellite electrode 604 to the hub 602.

In addition, the hub 602 of the biomedical sensor system 600 does not include an additional electrode. As a result, in order to be configured for a 3-lead ECG, the biomedical sensor system 600 includes three satellite electrodes 604. The hub 602 can be coupled to a subject, for example, by employing a similar adhesive to that employed by the satellite electrodes 604 (e.g., a pressure-sensitive adhesive), or the hub 602 can be positioned near the subject, without being coupled to the subject. Whether the hub 602 is coupled to the subject, the hub 602 can remain near the subject in use to allow the biomedical sensor system 600 to maintain a low profile and to conform to the subject.

For the sake of clarity and simplicity, one connector 606 will be described, but it should be understood that the description equally applies to all of the connectors 606 of the biomedical sensor system 600. The connector 606 is substantially comprised of a conductor 662, which includes an insulating coating or sheath that encapsulates and insulates the conductor 662 from the environment. As shown in FIG. 7, for example, the conductor 662 is adapted to be wound around a spool positioned at the hub 602, such that the connector 606 can be moved radially and angularly with respect to the hub 602 to position the respective electrode 604 in the desired position for accurate data acquisition. For example, the connector 606 can include a yo-yo configuration.

A variety of connector reel designs can be employed to achieve the biomedical sensor system 600 illustrated in FIG. 7. For example, in some embodiments, the connectors 606 can all be wound around a common spool at the hub 602. In some embodiments, the connectors 606 can each be wound around an independent spool, such that the winding of each connector 606 is independent of the winding of another connector 606. In some embodiments, the connectors 606 are retractable into and out of the hub 602, for example, by employing a winding roll, reel or spool that includes a cammed surface and a biasing force to maintain the connector 606 in various discrete positions and desired lengths. No matter what type of winding or retractable mechanism is employed, the biomedical sensor system 600 can be configured such that the connector 606 includes the winding mechanism, or the hub 602 includes the winding mechanism.

The connector 606 has a variable length by virtue of being wound or retracted (e.g., at the hub 602) to allow the electrode 604 to be moved toward and away from the hub 602. Each of the satellite electrodes 604 is shown in a first position $P_1'''$ nearer the hub 602 and a second position $P_2'''$ farther away from the hub 602. As demonstrated by the first and second positions $P_1'''$, $P_2'''$ of the electrode 604, the electrode 604 can be moved radially toward and away from the hub 602 due at least in part by extending the connector 606 (e.g., by unwinding a desired amount of the connector 606). In addition, each of the second positions $P_2'''$ is shown in FIG. 7 as being located an angular distance from each of the respective first positions $P_1'''$ to illustrate the ability of the connectors 606 to move the electrodes 604 radially and angularly with respect to the hub 602. However, each electrode 604 can also be moved substantially only radially or substantially only angularly with respect to the hub 602 and need not always be moved radially and angularly, depending on the winding mechanism employed in the connector 606 and/or the hub 602.

Figure 8:
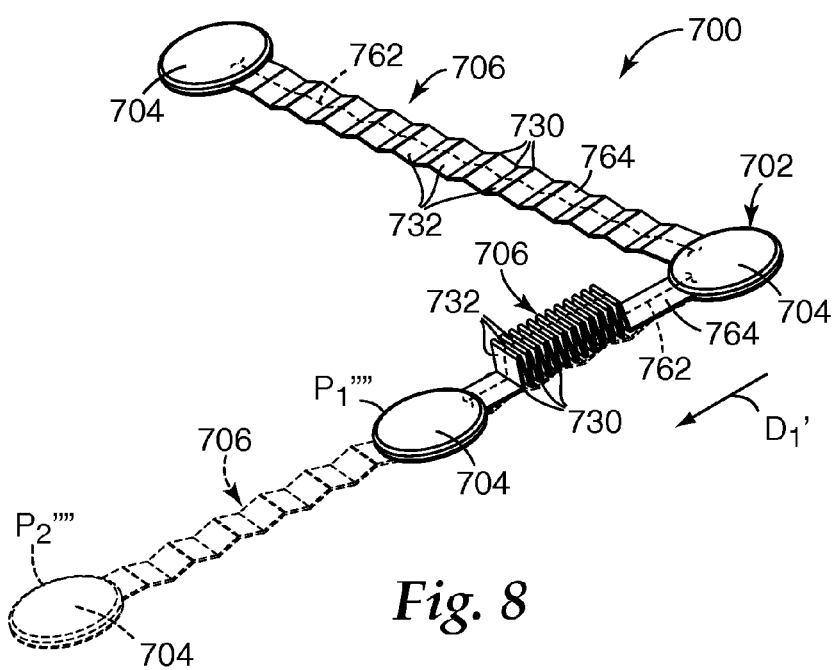
FIG. 8 is a perspective view of a biomedical sensor system according to another embodiment of the present disclosure.

FIG. 8 illustrates a biomedical sensor system 700 according to another embodiment of the present disclosure, wherein like numerals represent like elements. The biomedical sensor system 700 shares many of the same elements and features described above with reference to the illustrated embodiment of FIGS. 1-2. Accordingly, elements and features corresponding to elements and features in the illustrated embodiment of FIGS. 1-2 are provided with the same reference numerals in the 700 series. Reference is made to the description above accompanying FIGS. 1-2 for a more complete description of the features and elements (and alternatives to such features and elements) of the embodiment illustrated in FIG. 8.

Similar to the biomedical sensor system 100 illustrated in FIG. 1, the biomedical sensor system 700 is configured to produce a 3-lead ECG. As shown in FIG. 8, the biomedical sensor system 700 includes a hub 702, two satellite electrodes 704, and two connectors 706 positioned to mechanically and electrically couple each satellite electrode 704 to the hub 702.

Similar to the biomedical sensor systems 100 and 500 illustrated in FIGS. 1 and 6, respectively, and described above, the hub 702 includes an additional electrode 704, such that the biomedical sensor system 700 can take up less total surface area on the subject. In such embodiments, the hub 702 and the two satellite electrodes 704 can each be adapted to be coupled to skin.

For the sake of clarity and simplicity, one connector 706 will be described, but it should be understood that the description equally applies to all of the connectors 706 of the biomedical sensor system 700. The connector 706 includes a support member 764 to provide the mechanical coupling between the hub 702 and the electrode 704, and one or more conductors 762 positioned within the support member 764 to provide the communication pathway (e.g., for electrical communication) between the hub 702 and the electrode 704. Particularly, the support member 764 (and conductor(s) 762) includes a plurality of alternating folds or bends 730 that define sections 732 of the support member 764 and the connector 706.

The sections 732 of the support member 764/connector 706 can be collapsed upon one another to decrease the length of the connector 706, or the sections 732 can be extended apart from one another to increase the length of the connector 706. As a result, at least a portion of the connector 706 can include an accordion-style configuration, and the length of the connector 706 can vary, depending on the angle between adjacent sections 732 of the connector 706. For example, the adjacent sections 732 of the connector 706 can be positioned relatively close to one another when the folds 730 are folded to a low-angle position, and the adjacent sections 732 of the connector 706 can be positioned further apart from one another when the folds 730 are extended to a high-angle position.

As shown in FIG. 8, one electrode 704 is shown in a first position $P_1''''$ when the connector 706 is collapsed, and a second position $P_2''''$ (shown in phantom lines) when the connector 706 is extended. As a result, the electrode 704 is positionable toward and away from the hub 702 due at least in part to the variable-length connector 706. Similar to other embodiments described above, the electrode 704 is movable radially with respect to the hub 702, without being substantially movable angularly with respect to the hub 702.

The electrode 704 can be positioned intermediately of the first position $P_1''''$ and the second position $P_2''''$. In such positions, the connector 706 can remain substantially low-profile and conformable to a subject by maintaining any of the unused or unextended portions of the connector 706 in a collapsed state (i.e., by maintaining a low angle between adjacent sections 732 of the unused portion of the connector 706) to minimize any slack in the connector 706.

In some embodiments, the connector 706 can include an adhesive (e.g., a pressure sensitive adhesive) between adjacent sections 732 of the connector 706, such that the connector 706 can be maintained in a compressed configuration until enough force is applied to the connector 706 substantially along the length of the connector 706 (e.g., radially away from the hub 702 and substantially in a first direction $D_1'$) to overcome the peel force of the adhesive.

In the embodiment illustrated in FIG. 8, the folds 730 are oriented substantially vertically (e.g., in an x-z plane). However, it should be understood that other configurations or orientations of the folds 730 can also be employed, such that the folds 730 are oriented substantially horizontally (e.g., in an x-y plane), or the folds 730 can include a combination of a vertical and a horizontal orientation.

The distance between each adjacent fold 730 (i.e., the length of each section 732) of the connector 706 can be sized as necessary for a given application. For example, in some embodiments, the distance between each adjacent fold 730 in the connector 706 is relatively short, such that when the electrode 704 is positioned in its first position $P_1''''$, the height of the connector 706 is low enough to allow the connector 706 to conform to a subject and to maintain a relatively low profile.

The support member 764 and the conductor 762 can take on any of the forms described above with respect to the connectors 106, 206, 306, 406, 506 and 606, or combinations thereof. That is, the conductor 762 can be housed within an interior of the support member 764, or the conductor 762 can be embedded within the support member 764, the conductor 762 can include a plurality of bends, the conductor 762 can be substantially straight with respect to the support member 764, the conductor 762 can be positioned in between two support members 764, or a combination thereof.

In addition, the support member 764 can be formed of a variety of materials, including the materials described above with respect to the support members 164, 264, 364, and 464. In some embodiments, the conductor 762 is a flat piece of conductive material (e.g., a conductive metal, carbon ribbon, other suitable conductive materials, and combinations thereof) that folds and bends to form the accordion-style configuration and includes at least a thin layer or sheath of an insulating coating to encapsulate and insulate the conductive material. In such embodiments, the support member 764 can include the insulating coating or sheath.

In some embodiments, the connector 706 can include a rolled configuration, rather than an accordion-style configuration, such that a variable length of the connector 706 can be unrolled, rather than unfolded, to move the respective electrode 704 toward and away from the hub 702.

Figure 9:
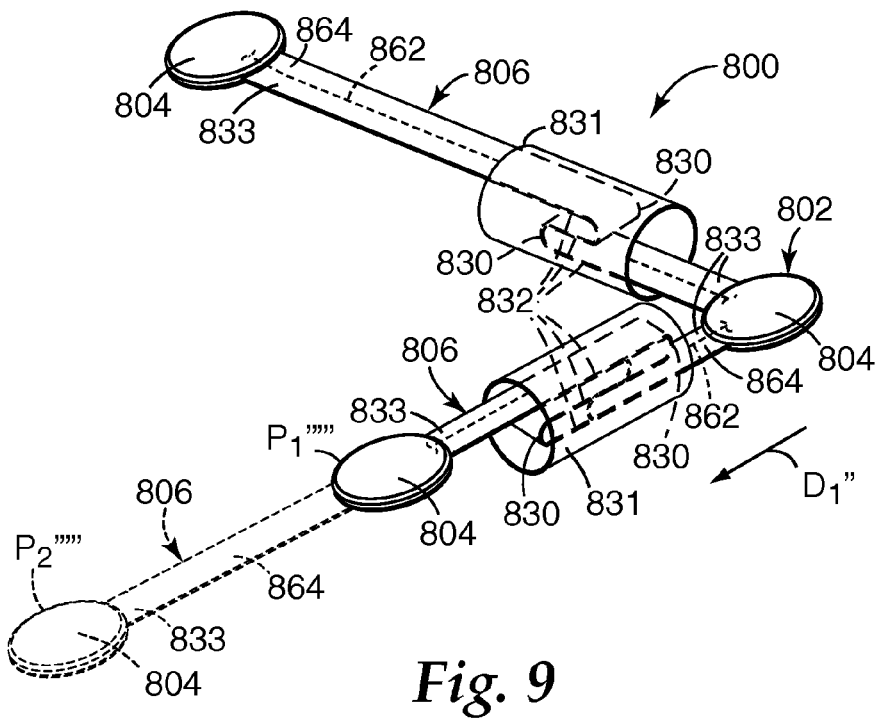
FIG. 9 is a perspective view of a biomedical sensor system according to another embodiment of the present disclosure.

FIG. 9 illustrates a biomedical sensor system 800 according to another embodiment of the present disclosure, wherein like numerals represent like elements. The biomedical sensor system 800 shares many of the same elements and features described above with reference to the illustrated embodiment of FIGS. 1-2. Accordingly, elements and features corresponding to elements and features in the illustrated embodiment of FIGS. 1-2 are provided with the same reference numerals in the 800 series. Reference is made to the description above accompanying FIGS. 1-2 for a more complete description of the features and elements (and alternatives to such features and elements) of the embodiment illustrated in FIG. 9.

Similar to the biomedical sensor system 100 illustrated in FIG. 1, the biomedical sensor system 800 is configured to produce a 3-lead ECG. As shown in FIG. 9, the biomedical sensor system 800 includes a hub 802, two satellite electrodes 804, and two connectors 806 positioned to mechanically and electrically couple each satellite electrode 804 to the hub 802.

Similar to the biomedical sensor systems 100 and 500 illustrated in FIGS. 1 and 6, respectively, and described above, the hub 802 includes an additional electrode 804, such that the biomedical sensor system 800 can take up less total surface area on the subject. In such embodiments, the hub 802 and the two satellite electrodes 804 can each be adapted to be coupled to skin.

For the sake of clarity and simplicity, one connector 806 will be described, but it should be understood that the description equally applies to all of the connectors 806 of the biomedical sensor system 800. The connector 806 includes a support member 864 to provide the mechanical coupling between the hub 802 and the electrode 804, and one or more conductors 862 positioned within the support member 864 to provide the communication pathway (e.g., for electrical communication) between the hub 802 and the electrode 804. Particularly, the support member 864 (and conductor(s) 862) includes one or more folds or bends 830 in between ends 833 that are coupled to the hub 802 and the electrode 804. The support member 864 (and conductor(s) 862) is folded lengthwise upon itself into overlapping sections 832 of the support member 864 and the connector 806.

As shown in FIG. 9, in some embodiments, the biomedical sensor system 800 can further include a sheath 831 that can form a portion of the connector 806 or be used in conjunction with the connector 806. The sheath 831 surrounds at least a portion of the folded sections 832 of the support member 864 but allows access to the ends 833 of the support member 864 (and conductor(s) 862). In this way, the sheath 831 can consolidate the unused portions of the support member 864, which can reduce slack in the overall connector 806, can minimize potential entanglement, and can improve conformability of the connector 806 (and biomedical sensor system 800) to a subject. In some embodiments, the entire folded sections 832 can be concealed by the sheath 831, and in some embodiments, at least a portion of the folded sections 832 can extend at least partially beyond the ends of the sheath 831.

The sections 832 of the support member 864/conductor 862 can be collapsed upon one another to decrease the length of the connector 806 until a greater length is desired. At that time, the ends 833 can be pulled with sufficient force to cause the support member 864/conductor 862 to slide within the sheath 831, thereby reducing the length of the folded portion of the support member 864/conductor 862 and increasing the overall length of the connector 806, which increases the distance between the hub 802 and the respective electrode 804. As a result, at least a portion of the connector 806 can include an accordion-style configuration, particularly, a lengthwise accordion-style configuration, and the length of the connector 806 can vary, depending on the length of the folded sections 832 of the support member 864/conductor 862.

As shown in FIG. 9, one electrode 804 is shown in a first position $P_1''''$ when the connector 806 is collapsed, and a second position $P_2''''$ (shown in phantom lines) when the connector 806 is extended. As a result, the electrode 804 is positionable toward and away from the hub 802 due at least in part to the variable-length connector 806. Similar to other embodiments described above, the electrode 804 is movable radially with respect to the hub 802, without being substantially movable angularly with respect to the hub 802.

The electrode 804 can be positioned intermediately of the first position $P_1''''$ and the second position $P2''''$. In such positions, the connector 806 can remain substantially low-profile and conformable to a subject by maintaining any of the unused or unextended portions of the connector 806 in a folded state and/or within the sheath 831 to minimize any slack in the connector 806.

In some embodiments, the connector 806 can include an adhesive (e.g., a pressure sensitive adhesive) between adjacent sections 832 of the connector 806, such that the connector 806 can be maintained in a folded configuration until enough force is applied to the ends 833 of the support member 864/conductor 862 substantially along the length of the connector 806 (e.g., radially away from the hub 802 and substantially in a first direction $D_1''$) to overcome the peel force of the adhesive.

In the embodiment illustrated in FIG. 9, the folded sections 832 are oriented substantially longitudinally with respect to the length of the connector 806. However, it should be understood that other configurations or orientations of the folded sections 832 can also be employed, such as the accordion-style configurations of the biomedical sensor system 700 shown in FIG. 8, or alternatives thereof described above.

By way of example only, in the embodiment illustrated in FIG. 9, the support member 864 includes two longitudinal folds 830 that form three overlapping folded sections 832. However, the number of folds 830 and the overall folding scheme or arrangement of folds 830 can be varied as necessary for a given application. For example, in some embodiments, a greater extension ratio is needed in the connector 806; however, this needs to be balanced with the overall volume or profile of the sheath 831 and the folded sections 832 of the connector 806. Exemplary alternative folding schemes are illustrated in FIGS. 10 and 11.

Figure 10:
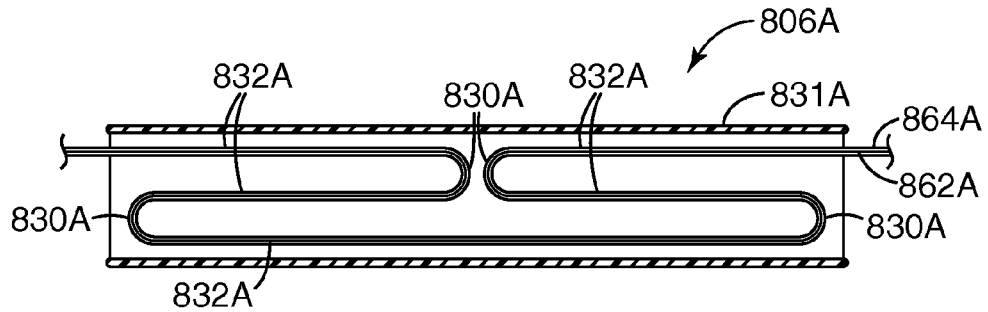
FIG. 10 is a cross-sectional view of a connector according to one embodiment of the present disclosure.
Figure 11:
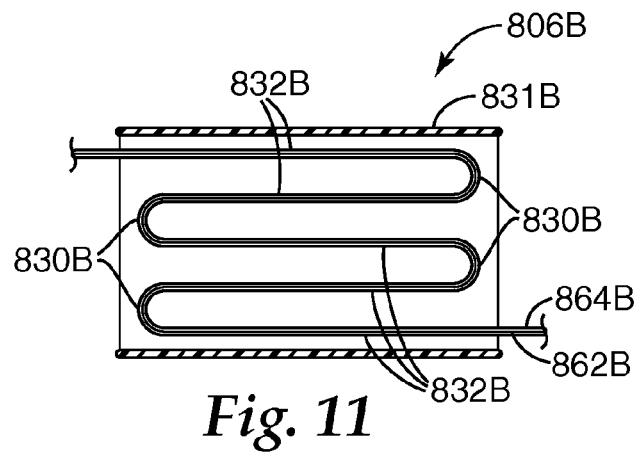
FIG. 11. is a cross-sectional view of a connector according to another embodiment of the present disclosure.

FIG. 10 illustrates a connector 806A in which the folded portion of the support member 864A/conductor 862A that is positioned within a sheath 831A can include four upper, shorter folded sections 832A stacked upon one lower and longer folded section 832A. Such a configuration can be formed, for example, by making four folds 830A in the support member 864A/conductor 862A. FIG. 11 illustrates another connector 806B in which the folded portion of the support member 864B/conductor 862B this is positioned within the sheath 831B can include four folds 830B and five folded sections 832B to increase the extension capability of the connector 806B (e.g., as compared to a connector 806 that includes a similarly dimensioned sheath 831 and only three folded sections 832).

With continued reference to FIG. 9, the sheath 831 can be formed of a variety of materials, including, but not limited to, metal, polymer, textiles, or combinations thereof. For example, in some embodiments, the sheath 831 can be formed of an elastic material (e.g., a polymer, a textile, or a combination thereof); a crimpable material (e.g., a metal); heat shrink tubing; a cast-on or brushed-on elastomer; other suitable materials adapted to hold the folded sections 832 firmly while allowing them to slide freely when a tensile force is applied to the ends 833 of the support member 864/conductor 862; or a combination thereof.

In addition, in some embodiments, the sheath 832 and/or the support member 864/conductor 862 can include a low friction material or can be lubricated to reduce the sheath-support member/conductor interfacial friction. Examples of lubrication can include, but are not limited to, externally-applied dry, liquid, or paste lubricants, lubricants embedded in one or both of the support member 864 and the sheath 831, forming one or both of the support member 864 and the sheath 831 of a low friction material (i.e., a material having a low coefficient of friction), or combinations thereof.

In some embodiments of the biomedical sensor system 800, one or a plurality of connectors 806 can be employed to connect one electrode 804 to the hub 802. In embodiments employing a plurality of connectors 806 associated with one electrode 804, the connectors 806 can be connected in series, parallel, or a combination thereof.

In some embodiments, the support member 864 can be extended and pulled from the sheath 831 to increase the length of the connector 806 but cannot be retracted or easily reinserted into the sheath 831 to decrease the length of the connector 806. However, in some embodiments, the support member 864 and/or the sheath 831 can be adapted to facilitate moving the support member 864 into and out of the sheath 831, and into and out of being in a folded configuration, such that the length of the connector 806 can be easily increased or decreased.

The support member 864 and the conductor 862 can take on any of the forms described above with respect to the connectors 106, 206, 306, 406, 506 and 606, or combinations thereof. That is, the conductor 862 can be housed within an interior of the support member 864, or the conductor 862 can be embedded within the support member 864, the conductor 862 can include a plurality of bends, the conductor 862 can be substantially straight with respect to the support member 864, the conductor 862 can be positioned in between two support members 864, or a combination thereof.

The support member 864 can be formed of a variety of materials, including the materials described above with respect to the support members 164, 264, 364, and 464. In some embodiments, the conductor 862 is a flat piece of conductive material (e.g., a conductive metal, carbon ribbon, other suitable conductive materials, and combinations thereof) that folds and bends to form the folded sections 832 and includes at least a thin layer or sheath of an insulating coating to encapsulate and insulate the conductive material. In such embodiments, the support member 864 can include the insulating coating or sheath.

In some embodiments, the connector 806 can include a rolled configuration, rather than a folded configuration, such that a variable length of the connector 806 can be unrolled, rather than unfolded, to move the respective electrode 804 toward and away from the hub 802.

Figure 12A:
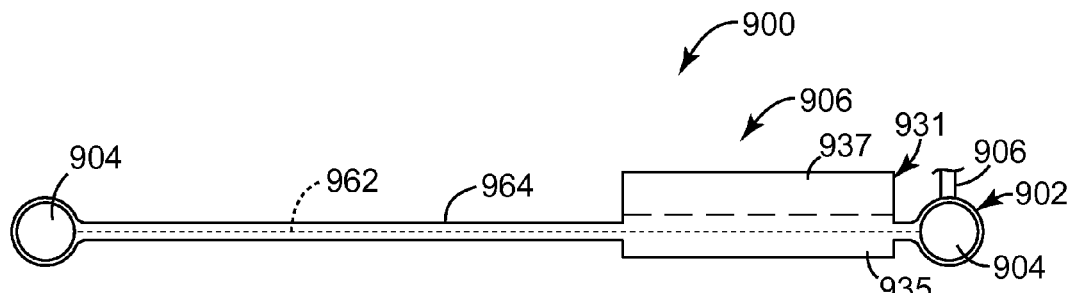
FIGS. 12A-12C illustrate top views of a biomedical sensor system according to another embodiment of the present disclosure.
Figure 12B:
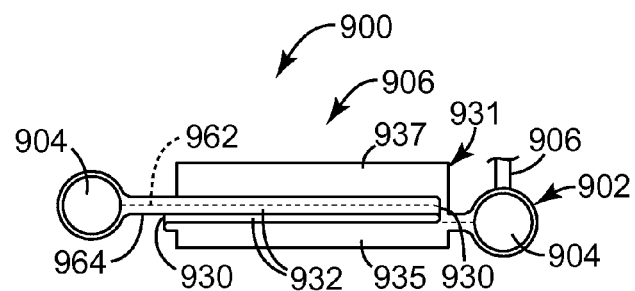
Figure 12C:
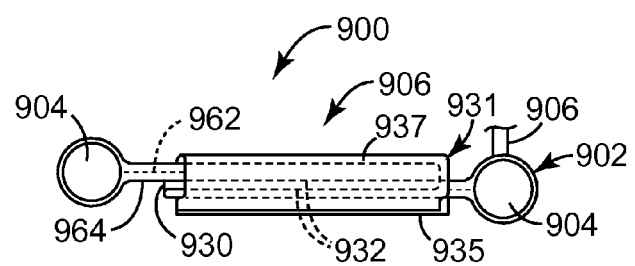

FIGS. 12A-12C illustrate a biomedical sensor system 900 according to another embodiment of the present disclosure, wherein like numerals represent like elements. The biomedical sensor system 900 shares many of the same elements and features described above with reference to the illustrated embodiments of FIGS. 9-11. Accordingly, elements and features corresponding to elements and features in the illustrated embodiments of FIGS. 9-11 are provided with the same reference numerals in the 900 series. Reference is made to the description above accompanying FIGS. 9-11 for a more complete description of the features and elements (and alternatives to such features and elements) of the embodiment illustrated in FIGS. 12A-12C.

As shown in FIGS. 12A-12C, the biomedical sensor system 900 includes a hub 902 (that includes an electrode 904) that is illustrated as being connected to multiple electrodes 904 via multiple connectors 906, with only one electrode 904 and connector 906 shown in detail, for simplicity and clarity. The connector 906 shown in FIGS. 12A-12C illustrates one example of making a variable-length connector 906, of which the folded or unextended portion can be covered by a sheath 931.

As shown in FIG. 12A, the sheath 931 is coupled to (e.g., integrally formed with) a support member 964 of the connector 906, and in its unwrapped state has a flat configuration. The sheath 931 includes a base portion 935 and a tab portion 937. In the embodiment illustrated in FIGS. 12A-12C, the tab portion 937 is larger than the base portion 935 and extends further from the remainder of the support member 964 than the base portion 935, but this configuration is shown by way of example only, and other configurations of the base portion 935 and the tab portion 937 can be appreciated by one of skill in the art.

As shown in FIG. 12B, the connector 906 further includes a conductor 962, and the support member 964 and/or the conductor 962 can be folded forming folds or bends 930. For example, the support member 964/conductor 962 can be folded (e.g., longitudinally) upon itself to decrease its length and to form one or more folded sections 932. The support member 964 can be folded up adjacent the flat sheath 931.

As shown in FIG. 12C, the sheath 931 can then be wrapped around the folded sections 932 of the support member 964. For example, the tab portion 937 can be wrapped around the folded sections 932 and coupled to the base portion 935 in order to form a sheath 931 that surrounds at least a portion of the folded sections 932 of the connector 906 but which allows the length of the connector 906 to vary to accommodate a given application, subject size, etc. In some embodiments, the entire folded sections 932 can be concealed by the sheath 931, and in some embodiments, as shown in FIG. 12C, at least a portion of the folded sections 932 can extend at least partially beyond the ends of the sheath 931.

The base portion 935 and the tab portion 937 can be coupled together via a variety of coupling means, including, but not limited to, press-fit or friction-fit engagement, snap-fit engagement, magnets, hook-and-loop fasteners, adhesives, cohesives, clamps, heat sealing, stitches, staples, screws, nails, rivets, brads, crimps, welding (e.g., sonic (e.g., ultrasonic) welding), any thermal bonding technique (e.g., heat and/or pressure applied to one or both of the components to be coupled), other suitable coupling means, or combinations thereof.

By way of example only, the embodiment illustrated in FIGS. 12A-12C can be formed by high-volume automated assembly applications, where the hub 902 (or a portion thereof), the electrode 904 (or a portion thereof), and the connector 906 can be fabricated by die-cut flex circuits.

Some embodiments of the biomedical sensor system of the present disclosure include connectors that allow an electrode to be moved away from a hub without allowing substantial return of the electrode toward the hub. That is, depending on the type of material employed in the connector, some connectors allow equal and opposite motion of the electrode to occur (e.g., some embodiments of the connectors 606 and 706), while in other connectors (e.g., some embodiments of the connectors 106, 206, 306, 406, and 506), at least above a certain threshold, at least some of the kinetic energy applied to the connector is taken up as viscous flow in the material (e.g., in the support member of the connector), causing the material to change shape (e.g., plastically deform) and elongate without substantial elastic recovery.

Any combinations of the above described biomedical sensor systems 100, 400, 500, 600, 700, 800, 900 can be employed. For example, one or more of the connectors 106, 206, 306, 406, 506, 606, 706, 806, 906 or combinations thereof, can be employed with one or more of the electrodes 104, 204, 404, 504, 604, 704, 804, 904 (or other sensors) and/or one or more of the hubs 102, 402, 502, 602, 702, 802, 902 in any orientation or configuration (e.g., 3-lead, 5-lead, 12-lead, etc.) to achieve a biomedical sensor system in which the one or more sensors are positionable by one or more variable-length connectors.

Method of Making

The biomedical sensor systems of present disclosure can be manufactured in a variety of manners, including modular designs. For example, in some embodiments, a hub, one connector, and one sensor are manufactured as one unit, and additional sensor-connector units can be coupled to the hub, as desired (e.g., to form a 3-lead, 5-lead, or 12-lead ECG configuration, etc.). In some embodiments, a hub is a separate unit, each sensor and connector are manufactured together as one unit, and each sensor-connector unit can be coupled to the hub or other sensor-connector units, as desired. Furthermore, in some embodiments, a hub and one or more connectors are manufactured as one unit, and the sensors can be added later (e.g., at the time of application to a subject). In some embodiments, each sensor, each connector, and a hub are formed individually to be completely modular, and the desired number of sensors, connectors and hubs are determined and coupled together later (e.g., at the time of application to a subject). Finally, in some embodiments, the hub, desired number of sensors, and desired number of connectors are formed as one unit for a specific application to allow the system to be applied with minimal pre-application coupling steps required.

Method of Applying

One exemplary method of applying a biomedical sensor system to a subject will be described, using the biomedical sensor system 500 illustrated in FIG. 6 by way of example only to illustrate how the biomedical sensor system 500 can be applied to a subject to acquire a 5-lead ECG. One of skill in the art will understand how the method of applying the biomedical sensor system 500 to a subject will apply to other embodiments of the biomedical sensor system of the present disclosure.

In some embodiments, the biomedical sensor system 500 can be applied to a subject by first dry-fitting the biomedical sensor system 500 to the subject. That is, the user (e.g., medical practitioner) can initially adjust the length of the connectors 506 without removing any liners from the hub 502 of electrodes 504 or activating any adhesives. To dry-fit the biomedical sensor system 500 to the subject, the user can hold the biomedical sensor system 500 in one hand and use the other hand to pull each of the electrodes 504 radially away from the hub 502 by extending the respective connectors 506 until the user has moved each electrode 504 to approximately its desired location for acquiring an ECG. The user can hold the biomedical sensor system 500 up to the subject before, during and/or after dry-fitting the biomedical sensor system 500 to visually verify the initial electrode positions.

After the user has dry-fit the biomedical sensor system 500, the user can first position the hub electrode 504 or one of the satellite electrodes 504 (e.g., by removing any liner and/or activating any adhesive at the hub 502 or satellite electrode 504). Then, the user can position the remaining electrodes 504, stretching each respective connector 506 more, if necessary, and being careful to extend each connector 506 sufficiently to minimize any tension on the subject (e.g., on the skin of the subject), while also minimizing slack in the connector 506.

The above method of applying the biomedical sensor system 500 is described by way of example only; however, it should be understood that a variety of other suitable methods can be employed to apply the biomedical sensor system of the present disclosure to a subject, and the present disclosure is not limited to the exact set or sequence of steps described above. In addition, as mentioned above, some embodiments of the biomedical sensor system of the present disclosure include modular components. As a result, it may be necessary for a user to assemble various components of the biomedical sensor system together prior to or during application to a subject. For example, in embodiments employing separate hub, connectors and sensors, the above steps can be proceeded by coupling (e.g., mechanically and/or to provide a communication pathway) one end of each connector to the hub and the opposite end of each connector to a sensor until the biomedical sensor system includes the desired number of connectors and sensors.

The following working examples are intended to be illustrative of the present disclosure and not limiting.

EXAMPLES

Example 1

A Connector Having an Electrical Pathway Before and After 500% Elongation

A sample of a 25-mil diameter solder wire (44 Rosin core, commercially available from Kester Inc., Glenview, Ill.) was cut to a length of 18 cm. A 15-cm section in the center, equidistant from both ends, was coiled over a 1-mm wire form and the pitch adjusted to obtain a coil having a length of 3 cm. The wire, serving as a conductor, was heat sealed in a linear low density polyethylene (LLDPE) film (Flexol ER276037), serving as a support member, so as to expose the two wire ends for electrical contact, and to form a connector. Two tabs were then affixed to the two ends of the heat-sealed film so as to partly cover the linear ends of the wire just outside of the coiled ends of the wire. The resistance across the wire was measured using a multimeter and registered at 1.3 ohms. The two tabs were then tightly grasped between the thumb and forefinger of each hand and the connector comprising the LLDPE laminate and the coiled wire was stretched to elongate the 3-cm section between the tabs to a length of 15 cm. During this process, the wire uncoiled and linearized. The resistance across the wire was measured again and was found to be unchanged at 1.3 ohms.

The embodiments described above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present disclosure. Various features and aspects of the invention are set forth in the following claims.

What is claimed is:

1. A biomedical sensor system comprising:
   a hub;
   a sensor adapted to create a signal based on a physiological characteristic from a subject, the signal comprising at least one of an electromagnetic signal and an electrical signal; and
   a connector coupled to the sensor, the connector adapted to be further coupled to the hub to provide a pathway between the hub and the sensor for the signal;
   wherein the connector comprises a viscoelastic support member having a variable length; and a conductor coupled to the support member, the conductor including at least one bend to accommodate the variable length of the viscoelastic support member; wherein the viscoelastic support member exhibits plastic deformation and has an elongation at break of at least 300%.

2. The biomedical sensor system of claim 1, wherein the sensor is a first sensor, the signal is a first signal, and the connector is a first connector, and further comprising:
   a second sensor adapted to create a second signal based on a physiological characteristic from the subject, the second signal comprising at least one of an electromagnetic signal and an electrical signal; and
   a second connector coupled to the second sensor, the second connector adapted to be further coupled to the hub to provide a pathway between the hub and the second sensor for the second signal, the second connector having a variable length.

3. The biomedical sensor system of claim 2, wherein the hub comprises a transceiver adapted to
   wirelessly transmit information to at least one of the first sensor, the second sensor, and downstream equipment;
   wirelessly receive information from at least one of the first sensor, the second sensor, and downstream equipment; and
   combinations thereof.

4. The biomedical sensor system of claim 1, wherein the sensor comprises an electrode.

5. The biomedical sensor system of claim 1, wherein the hub comprises an electrode.

6. The biomedical sensor system of claim 1, wherein the conductor is embedded within the support member.

7. The biomedical sensor system of claim 1, wherein the support member is a first support member and the connector further comprises a second support member, and wherein the conductor is coupled between the first support member and the second support member.

8. The biomedical sensor system of claim 1, wherein the support member defines an interior, and wherein the conductor is positioned within the interior of the support member.

9. The biomedical sensor system of claim 1, wherein the conductor is spiral or helical.

10. The biomedical sensor system of claim 1, wherein the conductor comprises an electrically conductive material.

11. The biomedical sensor system of claim 1, wherein the conductor comprises an optical fiber.

12. The biomedical sensor system of claim 1, wherein the support member includes at least one slit or weakened region.

13. The biomedical sensor system of claim 1, wherein the viscoelastic support member has an elongation at break of at least 500%.

14. The biomedical sensor system of claim 1, wherein the viscoelastic support member comprises a linear low density polyethylene.

15. A multi-lead ECG comprising:
   a hub;
   a first lead comprising
      a first satellite electrode adapted to create a first signal based on a physiological characteristic from a subject, the first signal comprising at least one of an electromagnetic signal and an electrical signal; and
      a first connector coupled to the first satellite electrode and adapted to be further coupled to the hub to provide a pathway between the hub and the first satellite electrode for the first signal, wherein the first connector has a variable length and comprises a first conductor coupled to a first support member, wherein the first support member is viscoelastic, has an elongation at break of at least 300%, and exhibits plastic deformation, and wherein the first conductor includes at least one bend to accommodate the variable length of the viscoelastic first support member;
   a second lead comprising
      a second satellite electrode adapted to create a second signal based on a physiological characteristic from the subject, the second signal comprising at least one of an electromagnetic signal and an electrical signal; and
      a second connector coupled to the second satellite electrode and adapted to be further coupled to the hub to provide a pathway between the hub and the second satellite electrode for the second signal, wherein the second connector has a variable length and comprises a second conductor coupled to a second support member, wherein the second support member is viscoelastic, has an elongation at break of at least 200%, and exhibits plastic deformation, and wherein the second conductor includes at least one bend to accommodate the variable length of the viscoelastic second support member; and
   at least a third electrode.

16. The multi-lead ECG of claim 15, wherein the third electrode is a third satellite electrode adapted to create a third signal based on a physiological characteristic from the subject, the third signal comprising at least one of an electromagnetic signal and an electrical signal, wherein the multi-lead ECG further comprises a third connector, the third connector coupled to the third satellite electrode and adapted to be further coupled to the hub to provide a pathway between the hub and the third satellite electrode for the third signal.

17. The multi-lead ECG of claim 15, wherein the hub comprises the third electrode.

18. A method of applying a biomedical sensor system to a subject, the method comprising:
  providing a biomedical sensor system comprising:
    a hub,
    a sensor, and
    a variable-length connector positioned to couple the sensor and the hub, the connector adapted to provide a pathway between the hub and the sensor for at least one of an electromagnetic signal and an electrical signal;
  changing the length of the variable-length connector to provide an appropriate distance between the sensor and the hub; and coupling the sensor to the subject;
  wherein the variable-length connector comprises a viscoelastic support member and a conductor coupled to the support member, the conductor including at least one bend to accommodate the variable length of the viscoelastic support member, and wherein changing the length of the connector comprises plastically deforming the viscoelastic support member.

* * * * *

UNITED STATES PATENT AND TRADEMARK OFFICE
CERTIFICATE OF CORRECTION

PATENT NO.        : 8,700,118 B2
APPLICATION NO.   : 12/990064
DATED             : April 15, 2014
INVENTOR(S)       : Oster et al.

Page 1 of 1

It is certified that error appears in the above-identified patent and that said Letters Patent is hereby corrected as shown below:

Title page
Item (56) References Cited under OTHER PUBLICATIONS
Line 2, "Streatchable" should read --Stretchable--.

Title page 2
Item (56) References Cited under OTHER PUBLICATIONS
Line 3, "[retrived" should read --[retrieved--.
Line 11, "[retrived" should read --[retrieved--.
Line 15, "[retrived" should read --[retrieved--.

In the Specification
Column 8
Lines 4-9 should be added after line 3 to continue the paragraph.
Line 51, "5-8004"" should read --S-8004"--.

Column 13
Line 67, "backing" should read --backing.--.

Column 15
Line 9, "thereof" should read --thereof.--.
Line 23, "(polyethylendioxythiophene)," should read --(polyethylenedioxythiophene),--.

Signed and Sealed this
Twenty-second Day of September, 2015

Michelle K. Lee
*Director of the United States Patent and Trademark Office*